United States Patent
Mihara et al.

(10) Patent No.: US 7,085,347 B2
(45) Date of Patent: Aug. 1, 2006

(54) RADIOTHERAPY DEVICE

(75) Inventors: Kazumasa Mihara, Hiroshima (JP); Kenji Hara, Hiroshima (JP); Ichiro Yamashita, Hiroshima (JP); Ikuo Wakamoto, Hiroshima (JP); Yuichiro Kamino, Aichi (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 101 days.

(21) Appl. No.: 10/416,016

(22) PCT Filed: Aug. 23, 2002

(86) PCT No.: PCT/JP02/08513

§ 371 (c)(1),
(2), (4) Date: May 9, 2003

(87) PCT Pub. No.: WO03/018133

PCT Pub. Date: Mar. 6, 2003

(65) Prior Publication Data
US 2004/0037390 A1    Feb. 26, 2004

(30) Foreign Application Priority Data

Aug. 24, 2001 (JP) .............................. 2001-254891
Aug. 24, 2001 (JP) .............................. 2001-254892

(51) Int. Cl.
*A61N 5/10* (2006.01)
*H05G 1/02* (2006.01)

(52) U.S. Cl. ........................................ 378/65; 378/197
(58) Field of Classification Search .................. 378/65, 378/68, 195–197, 17
See application file for complete search history.

(56) References Cited

U.S. PATENT DOCUMENTS 3,082,322 A * 3/1963 Koerner et al. ............... 378/65

(Continued)

FOREIGN PATENT DOCUMENTS

GB         1362678         8/1974

(Continued)

*Primary Examiner*—Edward J. Glick
*Assistant Examiner*—Thomas R. Artman
(74) *Attorney, Agent, or Firm*—Armstrong, Kratz, Quintos, Hanson & Brooks, LLP.

(57) ABSTRACT

The radiotherapy apparatus in the present invention includes a bed, a radiation irradiating head, head swing mechanisms, a precise inspection unit and a control unit. The bed carries a subject. The radiation irradiating head irradiates a treatment radiation to a treatment field of the subject. The head swing mechanisms, which are coupled to the radiation irradiating head, swings the head of the radiation irradiating head so that the treatment radiation emitted from the radiation irradiating head pursues the motion of the treatment field. The precise inspection unit obtains a diagnosis image containing the treatment field. The control unit controls the positions of the head swing mechanisms so that an irradiation field of the radiation irradiating head pursues the treatment field, based on the diagnosis image, the position of the radiation irradiating head and the state of the swung head. Then, the control unit controls the radiation irradiating head so that the treatment radiation is irradiated from the radiation irradiating head, after the positional control of the head swing mechanisms.

23 Claims, 21 Drawing Sheets

U.S. PATENT DOCUMENTS

| | | | |
|---|---|---|---|
| 5,008,907 A * | 4/1991 | Norman et al. | 378/65 |
| 5,207,223 A * | 5/1993 | Adler | 600/427 |
| 5,228,070 A | 7/1993 | Mattson | 378/19 |
| 5,427,097 A * | 6/1995 | Depp | 600/427 |
| 5,554,848 A | 9/1996 | Hermony et al. | 250/363.05 |
| 5,668,845 A | 9/1997 | Migita | 378/4 |
| 5,760,402 A * | 6/1998 | Hug et al. | 250/363.05 |
| 6,307,914 B1 | 10/2001 | Kunieda et al. | |
| 6,778,850 B1 * | 8/2004 | Adler et al. | 600/427 |
| 6,969,194 B1 * | 11/2005 | Nafstadius | 378/197 |

FOREIGN PATENT DOCUMENTS

| | | |
|---|---|---|
| JP | 52-18073 Y1 | 4/1977 |
| JP | 06-502330 | 3/1994 |
| JP | 08-504347 | 5/1996 |
| JP | 9-206391 A | 8/1997 |
| JP | 2000-167072 A | 6/2000 |
| WO | WO 92/06644 | 4/1992 |
| WO | WO 92/06644 A1 | 4/1992 |
| WO | WO 94/13205 | 6/1994 |
| WO | WO 94/13205 A1 | 6/1994 |
| WO | WO 00/07669 A1 | 2/2000 |

* cited by examiner

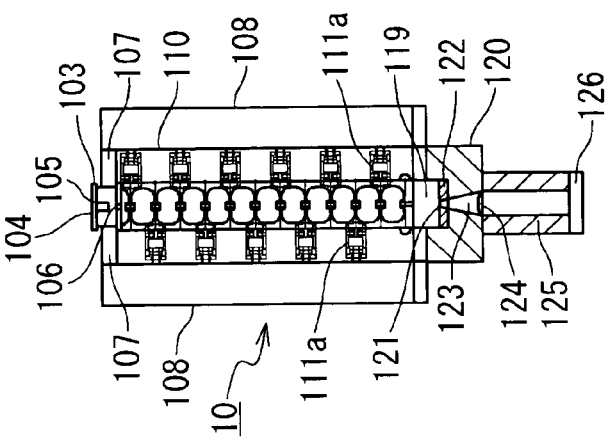
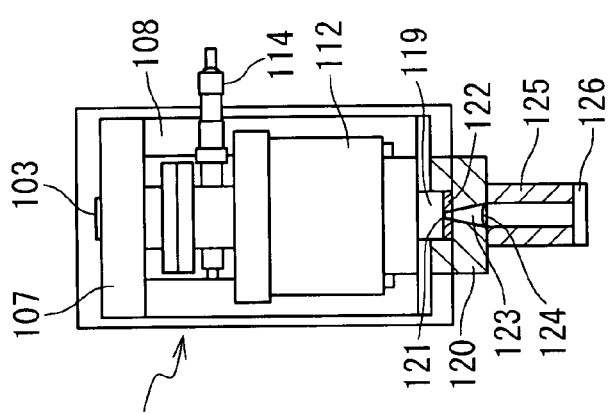
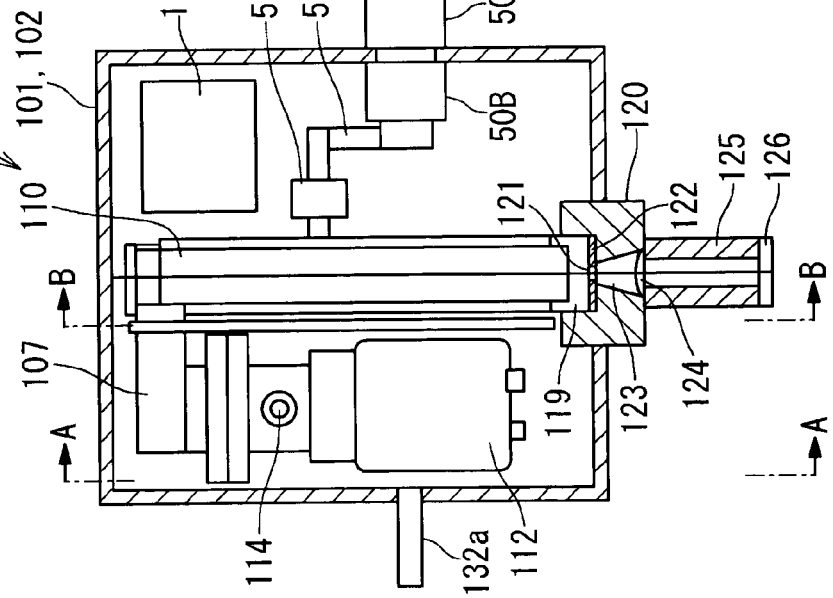

X-RAY BEAM DIRECTION

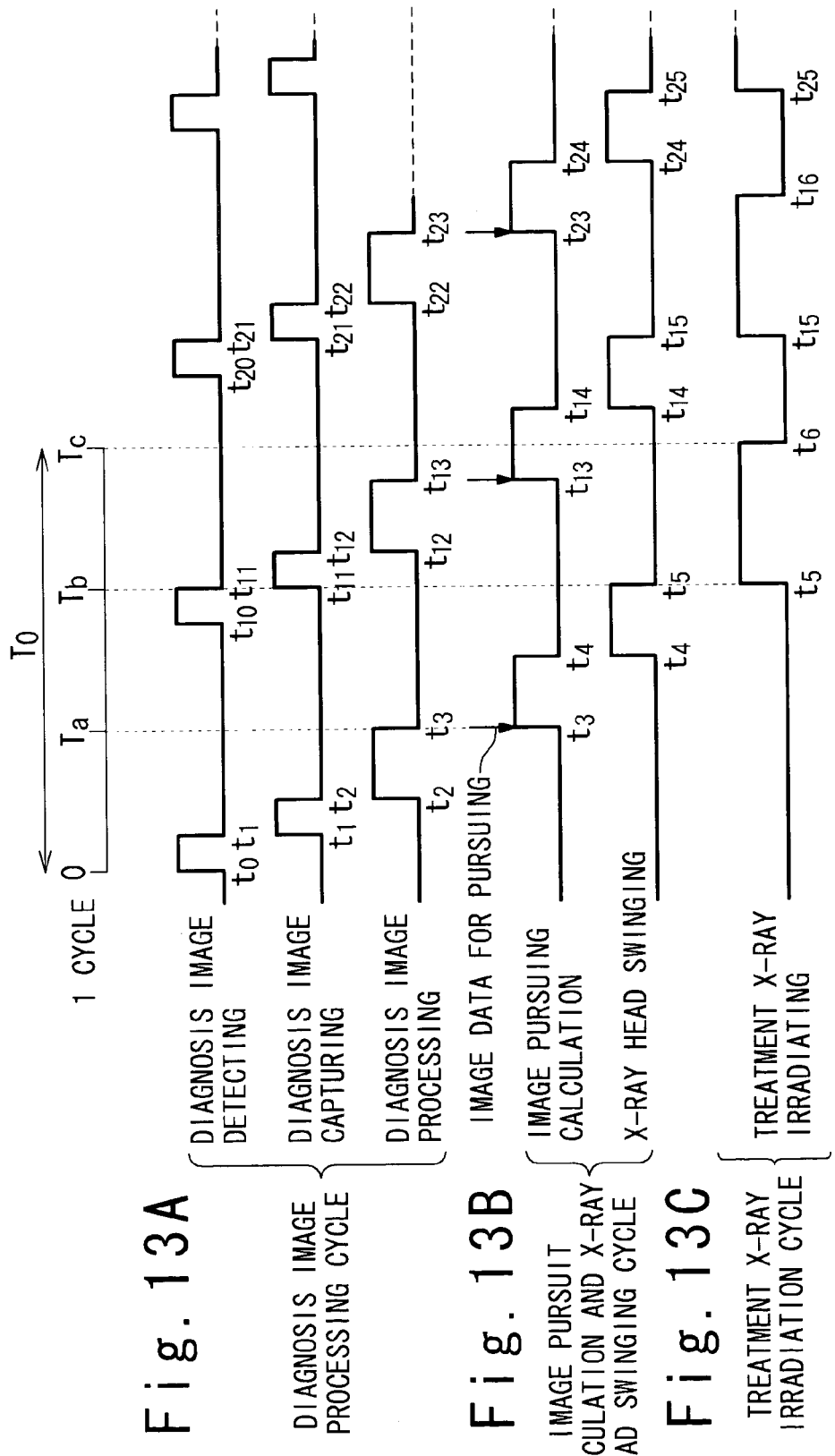

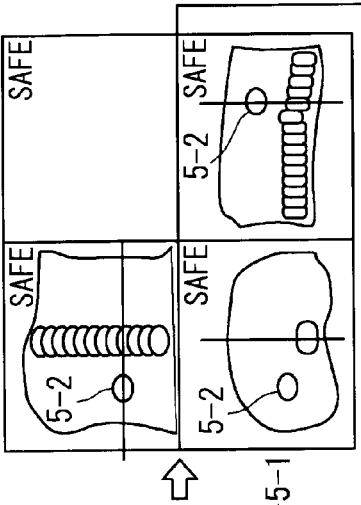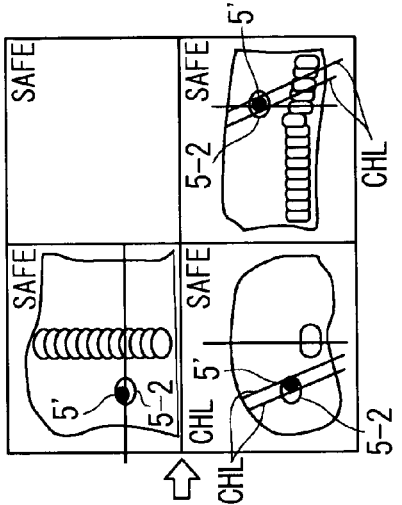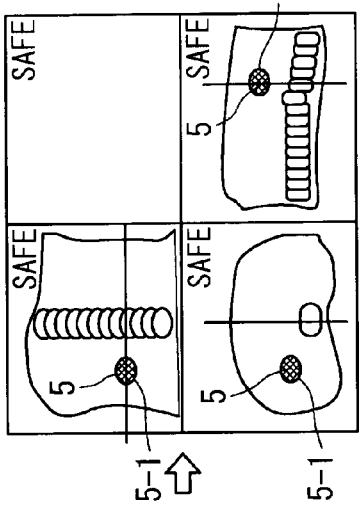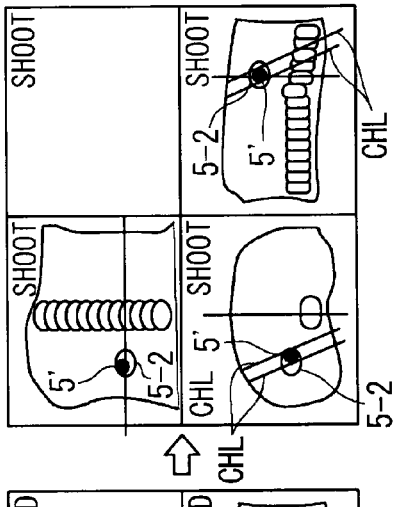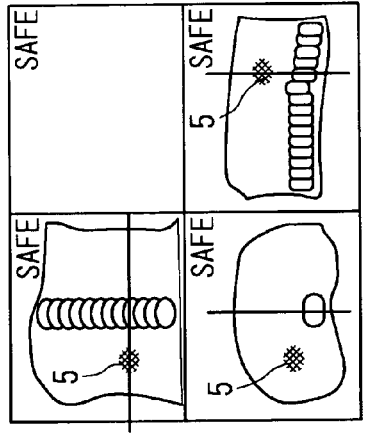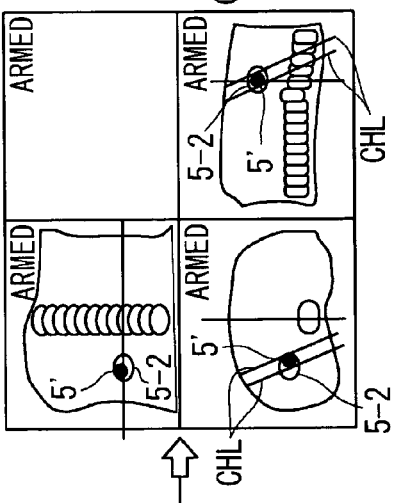

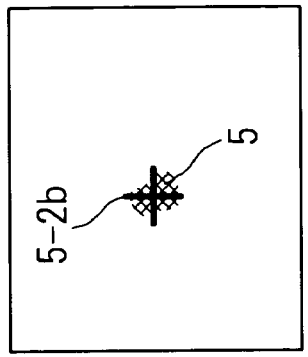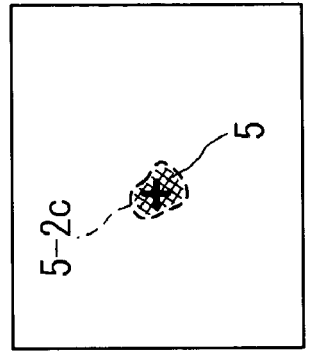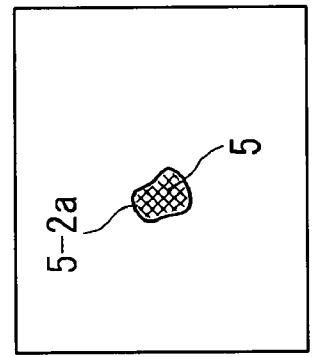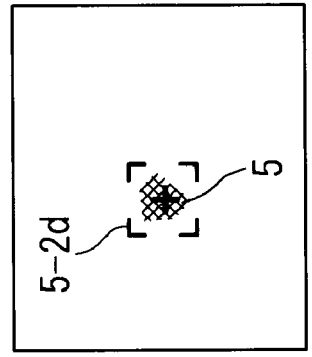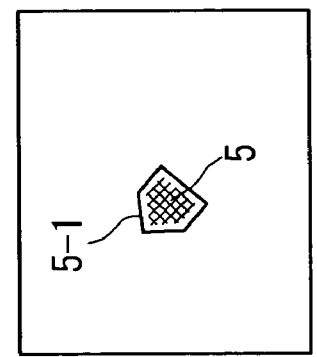

RADIOTHERAPY DEVICE

TECHNICAL FIELD

The present invention relates to a radiotherapy apparatus, and more particularly to a radiotherapy apparatus used for a stereotactic radiotherapy.

BACKGROUND ART

A radiotherapy apparatus for treating a cancer and a tumor by using radiation has been well known. As a three-dimensional irradiation radiotherapy apparatus for carrying out an irradiation at a stereotactic multiple arc, there are a radiosurgery treating apparatus, a linac (medical linear accelerator) treating apparatus and the like.

Here, the stereotactic multiple arc irradiation designates the radiotherapy method that intensively irradiates the radiation to a small focus from many directions and thereby improves the treatment effect, and further minimizes the exposure amount of ambient tissues. Its power is exerted on the treatment for a primary benign brain tumor, a single metastatic brain tumor whose size is 3 cm or less, a small lesion inside a brain such as a cranial base metastasis whose operation is difficult, an artery malformation, a vein malformation or the like.

The radiosurgery treating apparatus intensively irradiates a thin radioaction beam to a particular small region at a very high accuracy, from one or more radiation irradiating units fixed to the treating apparatus. As the radiation irradiating unit, a gamma-ray source or a linac are used.

In the radiosurgery treating apparatus, by using a precisely positioning/affected part immobilization device serving as an immobilization device for the stereotactic radiation irradiation, the affected part of a cranial bone of a patient and a part around the affected part are mechanically fixed. Then, by using this frame as a coordinate standard tool for the positioning, taking images for diagnosing such as X-ray CT (Computed Tomography), MRI, DAS (Digital Subtraction Angiography) and the like, is carried out to thereby deduce the accurate position and shape of the affected part. Then, the patient is mechanically fixed in an irradiating apparatus composed of: one or more radiation irradiating units; and a collimating mechanism for collimating them and concentrating the treating radiation on the small region in space, while this frame is kept. Consequently, the irradiation field is matched with the small region mechanically and precisely so that the stereotactic irradiation is precisely carried out. If a treatment field is spherical, a necessary treatment dosage can be irradiated at one time. If the treatment field is indeterminate, correspondingly to the shape of the treatment field, the positioning operation is repeated several times. At the same time, an aperture of a collimator is newly selected each time, and the irradiating treatment is carried out.

In the radiosurgery treating apparatus, the apparatus and the procedure are very simple, and the high reliability can be obtained. Together with them, if an irradiation target is not moved against the cranial bones such as a head portion, the positioning and irradiating operations can be extremely precisely performed. However, the irradiation field of the radiation irradiating unit is fixed, thus, the stereotactic irradiating treatment is not performed on the body part, in which the irradiation field at the tumor, the malformation and the like, is moved by the influence of the motion and the condition of organs such as a breath and a cardiac beat, a peristalsis, a urine amount within a urinary bladder and the like below a chin. Strictly, the radiation is not irradiated while the affected part is observed at real time.

In the linac treating apparatus, a large gantry rotates around one axis parallel to its installation surface by 360 degrees to thereby carry out an isocentric irradiating treatment. In addition, various irradiation can be carried out by adding the two-dimensional movement within vertical and horizontal planes of a treatment bed and the rotation within the horizontal plane. Also, by MLC (Multi Leaf Collimator), the irradiation field having a complex shape can be handled, and the precisely irradiating treatment (IMRT: Intensity Modulated Radio Therapy) can be carried out by controlling an irradiation dosage distribution.

The linac treating apparatus can not carry out a high speed position control. For this reason, a follow-up irradiation at real time can not be performed on the treatment field moving at a high speed, such as the movement caused by the cardiac beat. Also, a linac graphics through a transmission radiation of treatment X-rays is used as a monitor for the treatment field during the irradiation. Since the treatment X-ray has a property of a strong transmission and generates much scattered radiations, the image quality for the real time monitor in the irradiation field is not high.

A synchronous irradiation is performed by using a breath synchronizing apparatus in case of only a breathing motion. This can not image the image of the affected part at real time, thus, the position of the affected part is estimated by using a preset method. When the affected part is estimated to arrive at a preset irradiation position, the irradiating unit is triggered so as to carry out the treatment irradiation. As the estimating method, a marker put on the affected part is optically pursued. Or, the flow amount of exhalations is directly measured to grasp the breathing state of the patient to thereby estimate the movement of the affected part.

However, in the synchronous irradiation, the position of the affected part is estimated and the radiation is irradiated toward the estimated position. Thus, the radiation are not irradiated while the affected part is pursued at real time.

An apparatus for isocentrically driving an electron linac and an apparatus for driving an electron linac along a gantry having a preset shape are known as other three-dimensional irradiating radiotherapy apparatuses.

As the apparatus for isocentrically driving the electron linac, there is the apparatus including a small electron linac at a tip of an industrial general robot arm. The accurate shape and position of the affected part are deduced by correlating to a marker such as a small gold plate which is embedded as a sign near the affected part, and a landmark of the body organization such as a cranial bone and a breast, through an X-ray CT and MRI. Then, at the time of the treatment irradiation, the apparatus, while using two X-ray cameras with different visual lines and monitoring the motion of the landmark and then correcting a collimation, carries out the precise irradiation. This apparatus can essentially carry out the non-isocentric irradiating treatment through a freely moving performance of a six-degree-of-freedom robot arm.

Even though this apparatus uses a immobilization device for fixing the head part in a case of a treatment of the head part, it does not irradiate the radiation while directly observing the image of the affected part. That is, it does not photograph by using the X-ray camera during the irradiation of the treatment beam. For this reason, it employs the method of completing the photographing prior to the start of the irradiation, and confirming the irradiation position, and then starting the irradiation. Thus, also in this case, the irradiation field is not monitored at the real time. Also, since the electron linac is heavy in weight, the problems regarding the inertia and the like need to be solved, in order to perform the precise follow-up irradiation at the real time on the quick motion such as the cardiac beat while keeping the electron linac at the tip of the robot arm having cantilever structure.

Also, the industrial robot arm does not insure the absolute precision on a specified space coordinate, but it only insures a repetitive precision through teaching. Thus, the teaching and the work related thereto are required prior to the actual treatment.

The apparatus for driving the electron linac along the gantry having the preset shape is disclosed in, for example, Japanese Laid Open Patent Application (JP-A-Heisei 8-504347 (International Application Number: PCT/US93/11872)) and Japanese Laid Open Patent Application (JP-A-Heisei 6-502330) International Application Number: PCT/US91/07696)). This includes a C-arm type X-ray camera having two rotational axes and a medical electron linac similarly having two rotational axes. A three-dimensional irradiation can be carried out by further adding a different rotational axis to a conventional electron linac that can carry out only a rotation in one axis direction. The irradiating method is similar to the case of the radiosurgery treating apparatus in that it is isocentric and the head portion needs to be fixed by the frame. However, it is different from the case of the radiosurgery treating apparatus in that the large gantry is driven by the two axes.

The affected part of the patient is being moved even during the treatment. In particular, below the chin, the irradiation target such as the tumor or the like is always moved by the influence of the motion and the condition of the organs, such as the breath, the cardiac beat, the peristalsis and the urine amount within the urinary bladder. For example, only when the patient lies, the body becomes gradually flat. Moreover, although the breath and the cardiac beat that are cyclic motions are cyclic, the motions of the respective organs associated with the cyclic motions do not always pass through the same routes every time.

On the other hand, in order to accurately capture the motion of the irradiation target at the real time, it is said that a technique for photographing images at a rate of about 30 images per second is required since the cardiac beat that is one of the fastest motions is one to two times per second. Then, if accurately pursuing the irradiation target at the real time and irradiating the radiation, it is necessary to accurately train a radiation irradiating head on the irradiation target for each 1/30 second.

Even if the treatment field of the radiation is being moved, the technique is required which can irradiate the radiation while pursuing the treatment field. The technique is desired which can monitor the state of the treatment field at the real time. The technique is desired which can carry out the quick collimation adjustment from a region of a wide region and execute the radiation irradiation. And, the technique is desired which can reduce the burden of the radiation irradiation on the patient while improving the treatment effect.

Therefore, an object of the present invention is to provide a radiotherapy apparatus which can irradiate the radiation while pursuing the treatment field, even if the treatment field of the radiation is being moved.

Another object of the present invention is to provide a radiotherapy apparatus that can monitor the state of the treatment field at the real time even during the irradiation treatment of the radiation.

Still another object of the present invention is to provide a radiotherapy apparatus that can carry out the quick collimation adjustment from the region of the wide region and execute the radiation irradiation, as well as the irradiation around the single rotational axis and the isocentric irradiation.

Yet still another object of the present invention is to provide a radiotherapy apparatus that can accurately irradiate the radiation and meanwhile improve the treatment effect and reduce the burden on the patient.

DISCLOSURE OF INVENTION

The disclosure of the present invention will be described below by using reference numbers and symbols used in [Best Mode for Carrying out the Invention]. The reference numbers and the symbols are added together with parentheses in order to clarify the corresponding relation between the descriptions in [claims] and [Best Mode for Carrying out the Invention]. However, the reference numbers and the symbols must not be used to construe the technical range of the present invention noted in [claims].

Therefore, in order to solve the above-mentioned problems, the radiotherapy apparatus in the present invention includes a bed (7-2), a radiation irradiating head (10), head swing mechanisms (131, 132), a precise inspection unit (30) and a control unit (80).

The bed (7-2) carries a subject (4). The radiation irradiating head (10) irradiates a treatment radiation (3a) to a treatment field (5) of the subject (4). The head swing mechanisms (131, 132), which are linked (coupled) to the radiation irradiating head (10), swings the head of the radiation irradiating head (10) so that the treatment radiation (3a) emitted from the radiation irradiating head (10) pursues the motion of the treatment field (5). The precise inspection unit (30) obtains a diagnosis image containing the treatment field (5). The control unit (80) controls the positions of the head swing mechanisms (131, 132) so that an irradiation field (5') of the radiation irradiating head (10) pursues the treatment field (5), based on the diagnosis image, the position of the radiation irradiating head (10) and the state of the swung head.

Then, the control unit (80) controls the radiation irradiating head (10) so that the treatment radiation (3a) is irradiated from the radiation irradiating head (10), after the positional control of the head swing mechanisms (131, 132).

Also, in the radiotherapy apparatus of the present invention, the control unit (80) calculates first coordinates (X, Y, Z) as the coordinates of the treatment field (5) within the diagnosis image, in accordance with an image pattern (5-2) preliminarily specified on the diagnosis image indicative of the treatment field (5). Also, it calculates second coordinates (x, y, z) as the coordinate of the irradiation field (5') in accordance with the position of the radiation irradiating head (10) and the state of the swung head of the radiation irradiating head (10). Then, it controls the positions of the head swing mechanisms (131, 132) so that the treatment field (5) is contained in the irradiation field (5'), in accordance with the first coordinates (X, Y, Z) and the second coordinates (x, y, z).

Also, in the radiotherapy apparatus of the present invention, for each preset time interval, the control unit (80) controls the positions of the head swing mechanisms (131, 132) and controls the radiation irradiating head (10).

Also, in the radiotherapy apparatus of the present invention, the precise inspection unit (30) includes an X-ray source (97), a sensor array (98) and an image process unit (31).

The X-ray source (97) irradiates a diagnosis radiation (3b) to the treatment field (5) of the subject (4). The sensor array

(98) detects a transmitted radiation of the diagnosis radiation (3b) transmitted through the subject (4) and outputs as a diagnosis image data. The image process unit (31) generates the diagnosis image of the treatment field (5) in accordance with the diagnosis image data.

Also, in the radiotherapy apparatus of the present invention, in the precise inspection unit (30), the X-ray source (97) and the sensor array (98) are located at the positions that are point-symmetrical with an isocenter (5a). Then, the sensor array (98) is placed closer to the radiation irradiating head (10), as compared with the X-ray source (97).

Also, in the radiotherapy apparatus of the present invention, the precise inspection unit (30) includes a plurality of sets, each having the X-ray source (97) and the sensor array (98). Then, the image process unit (31) generates the diagnosis image of the treatment field (5) in accordance with the diagnosis image data outputted from each of the plurality of sets.

Also, the radiotherapy apparatus of the present invention further includes a guide rail (9) and a head circulation moving mechanism (68).

The guide rail (9) has an orbit on which the head swing mechanisms (131, 132) and the radiation irradiating head (10) are moved. The head circulation moving mechanism keeps the head swing mechanisms (131, 132) and the radiation irradiating head (10) at movable states and moves the head swing mechanisms (131, 132) and the radiation irradiating head (10) along the guide rail (9).

Also, in the radiotherapy apparatus of the radiotherapy apparatus, the guide rail (9) is placed so as to straddle the bed (7-2) in a width direction, and has a half-arc orbit.

Also, the radiotherapy apparatus of the present invention further includes a rail tilting mechanism (28) for tilting the guide rail (9) around a horizontal axis (26) within a range of a quarter spherical shell.

Also, in the radiotherapy apparatus of the present invention, the head swing mechanisms (131, 132) swing the head of the radiation irradiating head (10) around each of two axes (S1, S2) orthogonal to each other.

Also, the radiotherapy apparatus of the present invention further includes a microwave generating unit (70) and a waveguide (51).

The microwave generating unit (70) generates a microwave. One end of the waveguide (51) is connected to the microwave generating unit (70), and the other end is connected to the radiation irradiating head (10). Then, it guides the microwave to the radiation irradiating head (10).

Also, in the radiotherapy apparatus of the present invention, its microwave belongs to a C band.

Then, the radiation irradiating head (10) has an accelerating structure (110) for accelerating an electron ray through its microwave.

Also, in the radiotherapy apparatus of the present invention, its microwave belongs to an X band.

Then, the radiation irradiating head (10) has an accelerating structure (110) for accelerating an electron ray through its microwave.

In order to solve the above-mentioned problems, a radiotherapy method of the present invention includes the steps of: detecting a diagnosis image containing a treatment field (5) of a subject (4); defining a definition region (5-1) as the treatment field (5) from the diagnosis image; recognizing an image pattern (5-2) within the definition region (5-1); moving a radiation irradiating head (10) for irradiating a treatment radiation (3a) to the subject (4) so that an irradiation field (5') of the radiation irradiating head (10) pursues the treatment field (5); irradiating the treatment radiation (3a) to the irradiation field (5').

Also, in the radiotherapy method of the present invention, the step of moving the radiation irradiating head (10) includes the steps of: calculating first coordinates (X, Y, Z) indicative of the position of the image pattern (5-2), in accordance with the diagnosis image; calculating second coordinates (x, y, z) indicative of the position of the irradiation field (5'), in accordance with the position and the orientation of the radiation irradiating head (10); and moving the radiation irradiating head (10) so that the second coordinates (x, y, z) pursue the first coordinates (X, Y, Z), in accordance with the first coordinates (X, Y, Z) and the second coordinates (x, y, z).

In order to solve the above-mentioned problems, a program with regard to the present invention instructs a computer to execute a method of including the steps of: receiving a detected diagnosis image containing a treatment field (5) of a subject (4); recognizing an image pattern (5-2) of a definition region (5-1) defined as the treatment field (5), in the diagnosis image; controlling a radiation irradiating head (10) so that an irradiation field (5') of the radiation irradiating head (10) for irradiating a treatment radiation (3a) to the subject (4) pursues the treatment field (5); and controlling the radiation irradiating head (10) so as to irradiating the treatment radiation (3a) to the irradiation field (5').

Also, the program with regard to the present invention instructs the computer to execute the above-mentioned method, in which the step of controlling the radiation irradiating head (10) so that the irradiation field (5') pursues the treatment field (5) includes the steps of: calculating first coordinates (X, Y, Z) indicative of the position of the image pattern (5-2), in accordance with the diagnosis image; calculating second coordinates (x, y, z) indicative of the position of the irradiation field (5'), in accordance with the position and the orientation of the radiation irradiating head (10); and controlling the radiation irradiating head (10) so that the second coordinates (x, y, z) pursue the first coordinates (X, Y, Z), in accordance with the first coordinates (X, Y, Z) and the second coordinates (x, y, z).

The radiotherapy apparatus of the present invention can carry out the pseudo non-isocentric irradiation by adding the mechanisms (131, 132) for making the radiation irradiating head (10) carry out the small angular rotation (the head swinging) in the one-axis or two-axis direction, in addition to the mechanisms (9, 28) for positioning by isocentrically moving the radiation irradiating head (10) in the one-axis or two-axis direction. The non-isocentric component determined from the correspondence to the undefined irradiation field (5') and the follow-up to the movement of the irradiation field (5') is 50 mm or less in the irradiation field (5'). A distance SAD (Source Axis Distance) between the radiation source and the isocentric irradiation field (5') is a value between 80 cm and 100 cm, in the case of the typical electron linac. When the SAD is 100 cm, an angle of the small angular rotation (the head swinging) required of the radiation irradiating head (10) is about 3 degrees. Since the change of the SAD caused by this motion is 0.2%, the change of the beam diameter of the treatment radiation (3a) caused by the change of the SAD is in the negligible range. Also, the burden on the driving mechanism can be reduced by using a mechanism that carry out this rotation around the axis at the inertia center of the radiation irradiating head (10). The reaction associated with the small angular rotation (the head swinging) can be offset by driving a dummy weight of the same moment as the moment around the rotational axis of the radiation irradiating head (10), oppositely to the rotational direction.

The shape of the above-mentioned mechanism is thought out so as not to mechanically interfere with an imager (30) such as an X-ray camera, DSA (Digital Subtraction Angiography) and X-ray CT, and the imager (30) and the above-mentioned mechanism have the common position coordinates. Also, the timing control is carried out so as to carry out the image capture timing of the imager (30) and the irradiation timing of the treatment radiation (3a) at time sharing, consequently, the image of the treatment field can be monitored at the real time even during the treatment irradiation, while the influence on the imager (30) of the treatment radiation (3a) is avoided.

The follow-up irradiation treatment to the moving treatment field can be carried out by performing the image pursuit on the treatment field image at a proper algorithm under the monitor image (display) and then controlling the small angular rotation (the head swinging) with pursuing it.

Moreover, the radiotherapy apparatus that is high in security and reliability can be achieved by installing a proper man-machine interface and safety mechanism.

BRIEF DESCRIPTION OF DRAWINGS

FIG. 4A is an entire view showing a configuration of an X-ray head applied to the radiotherapy apparatus of the present invention;

FIG. 4B is a sectional view taking on the line A—A of FIG. 4A;

FIG. 4C is a sectional view taking on the line B—B of FIG. 4A;

FIG. 13A is a timing chart showing a timing of an operation for processing a diagnosis image, in an operation of an embodiment of the radiotherapy apparatus of the present invention;

FIG. 13B is a timing chart showing a timing of a head swing operation of an X-ray head and an image pursuit calculation based on a diagnosis image after the processing;

FIG. 13C is a timing of irradiating a treatment X-ray;

FIGS. 17A to 17F are flowcharts showing a procedure of a pseudo non-isocentric treatment by using indications on a display;

FIG. 18A is a view showing a relation between a affected part and a definition region, in a relation among the affected part, the definition region and a contour line through a pattern matching;

FIGS. 18B to 18E are views showing a relation between the affected part and the contour line;

BEST MODE FOR CARRYING OUT THE INVENTION

Embodiment of a radiotherapy apparatus of the present invention will be described below with reference to the attached drawings.

FIRST EMBODIMENT

A first embodiment of the radiotherapy apparatus of the present invention will be described below with reference to the attached drawings.

Figure 1:
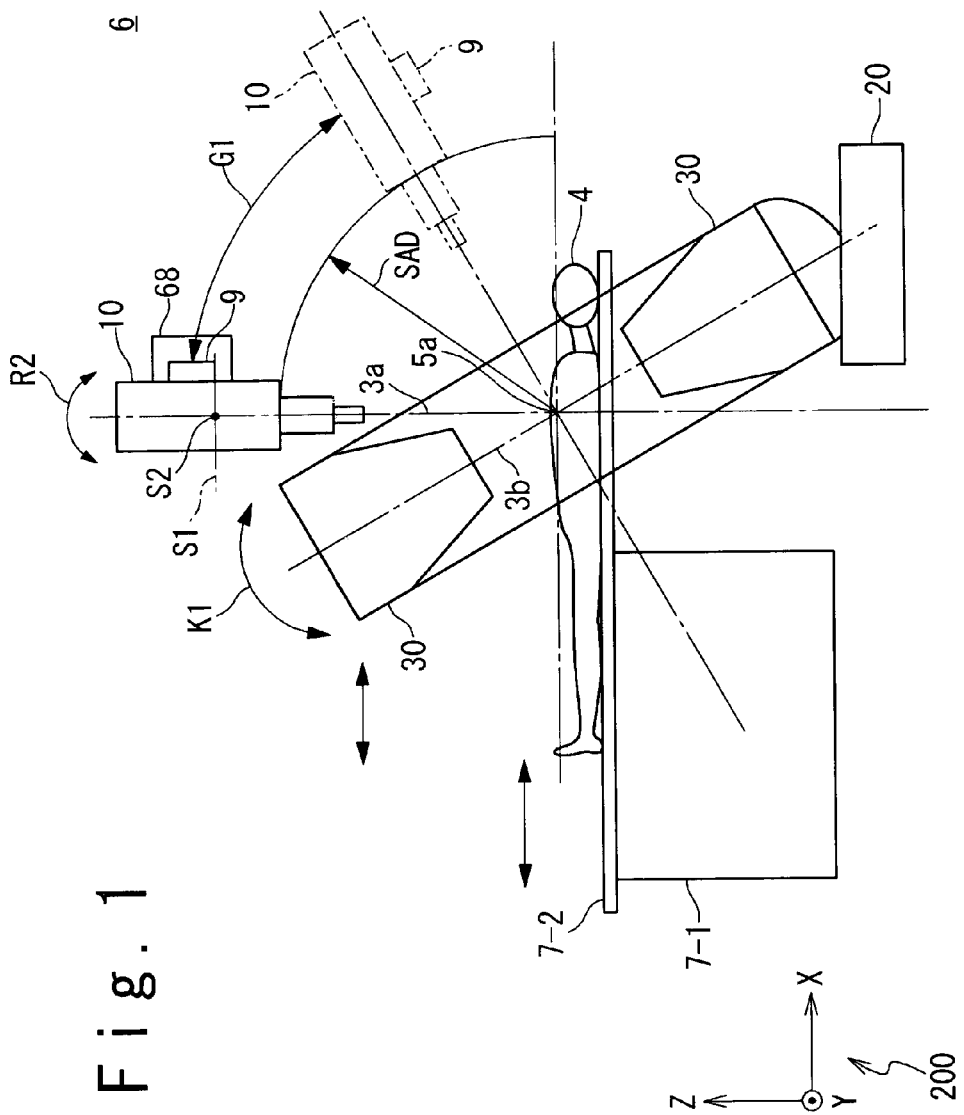
FIG. 1 is a side view showing a configuration in a first embodiment of a radiotherapy apparatus of the present invention.
Figure 2:
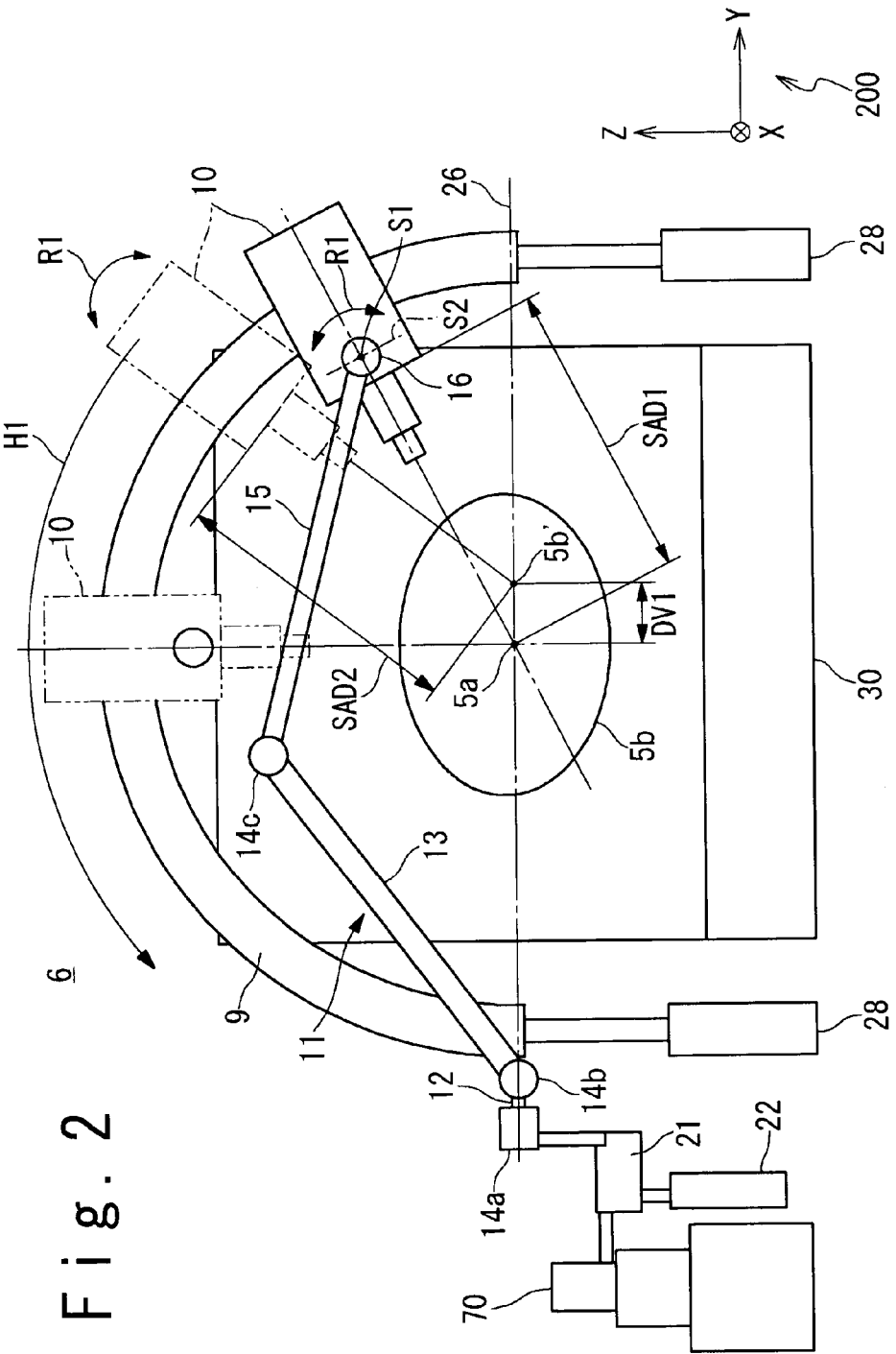
FIG. 2 is a front view showing the configuration of the first embodiment of the radiotherapy apparatus of the present invention.
Figure 3:
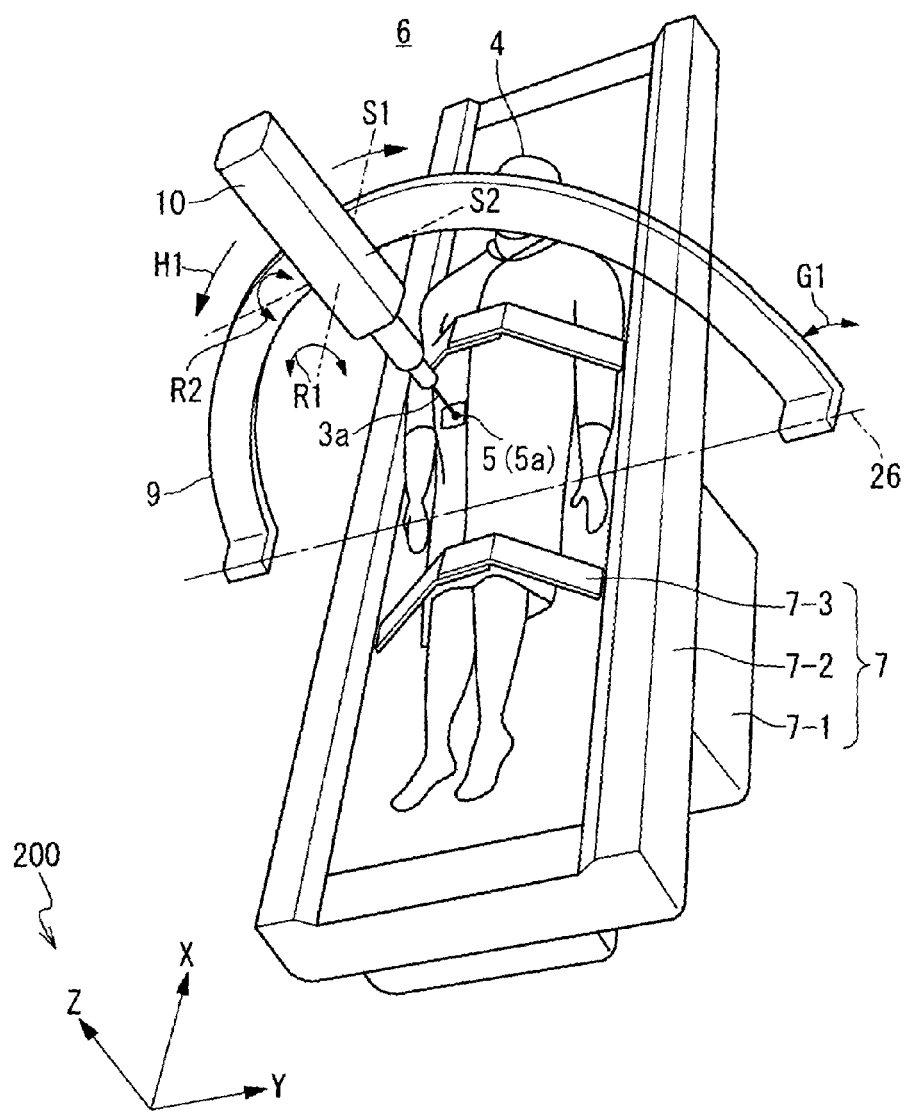
FIG. 3 is a perspective view showing the configuration of the first embodiment of the radiotherapy apparatus of the present invention.

FIGS. 1 to 3 are a side view, a front view and a perspective view showing the configuration in the first embodiment of the radiotherapy apparatus of the present invention. The parts thereof are omitted depending on the drawing. A coordinate 200 indicates a three-dimensional orthogonal coordinate having an X-axis, a Y-axis and a Z-axis in FIGS. 1 to 3.

A radiotherapy apparatus 6 includes a treatment bed system 7, an X-ray head 10, a first head swing mechanism 131, a second head swing mechanism 132, an arc guide rail 9, a microwave generating unit 70, a driven type waveguide system 11 and a real time imager 30.

The treatment bed system 7 has a bed driving system 7-1, a treatment bed 7-2 and a patient immobilization device 7-3.

The treatment bed 7-2 carries and moves a patient 4 on which radiotherapy is performed. It is put on an X-Y table of the treatment bed system 7. The patient immobilization device 7-3 fixes the patient 4 onto the treatment bed 7-2. The bed driving system 7-1 can move the treatment bed 7-2 in the three-axis directions of a length direction (an X-axis direction), a width direction (a Y-axis direction) and a height direction (a Z-axis direction) of the treatment bed 7-2, by using a built-in driving mechanism (not shown). Then, the bed driving system 7-1 adjusts the position of the treatment bed 7-2 so that a affected part 5 serving as an irradiation field 5' is located at an isocenter 5a in accordance with a diagnosis image data of the real time imager 30 (an X-ray CT inspecting unit in this embodiment) under the control of a system control unit 80 (which will be described later). The materials and the shapes suitable for the usage of an image diagnosing apparatus, such as the real time imager 30, a solid photographing device for X-ray (an X-ray CCD) and PET (Position Emission Tomography) are selected for the treatment bed 7-2 and the patient immobilization device 7-3.

The X-ray head 10 is a radiation irradiating head for irradiating a treatment X-ray 3a to the irradiation field 5 (the affected part 5). It includes a small electron linac for irradiating the treatment X-ray 3a. It is movably installed through a circulation moving mechanism 68 (described later) to the arc guide rail 9 (described later). It includes the first head swing mechanism 131 (described later) and the third head swing mechanism 132 (described later). The X-ray head 10 has a total length of 500 to 600 mm, a width of 500 mm, a depth of 300 mm and a weight of 60 to 80 kg.

The first head swing mechanism 131 is the mechanism for swinging (rotationally moving) the X-ray head 10 on the arc guide rail 9, as represented by R1 around the first swing axis S1. The first swing axis S1 is placed on an axis substantially penetrating an inertia center of the X-ray head 10 or in the vicinity thereof, so that the inertia becomes lower when the X-ray head 10 is swung.

The second head swing mechanism 132 is the mechanism for swinging (rotationally moving) the X-ray head 10 on the arc guide rail 9, as represented by R2 around the second swing axis S2. The second swing axis S2 is placed on the axis substantially penetrating the inertia center of the X-ray head 10 or in the vicinity thereof, so that the inertia becomes lower when the X-ray head 10 is swung.

The arc guide rail 9 has a guide rail tilting mechanism 28 and the circulation moving mechanism 68.

The arc guide rail 9 is placed so as to have a half-circle ring in a shape of an upper half arc from the treatment bed 7-2 and straddle the treatment bed 7-2. A guide rail tilting axis 26 is an axis in a Y-axis direction through which both ends and the center of the half-circle are coupled, and the center of the circle coincides with the isocenter 5a. This arc guide rail 9 is tiltably supported by the guide rail tilting mechanism 28. The guide rail tilting mechanism 28 tilts the arc guide rail 9 in a range between 0 degree (a position uprightly standing in a plus direction of the Z-axis) and 90 degrees (a position laterally fallen in a plus direction of the X-axis) around the guide rail tilting axis 26, as indicated by G1 of FIG. 1. That is, the arc guide rail 9 carries out the motion so as to draw a quarter ball (a quarter sphere) with the isocenter 5a as a center. The arc guide rail 9 is made of, for example, a material having a strong rigidity such as a stainless steel. Its width is 200 to 400 mm, its thickness is 20 to 50 mm, and its radius from the isocenter 5a is 800 to 1000 mm.

Also, the circulation moving mechanism 68 circularly moves the X-ray head 10 on the half arc of the arc guide rail 9 along the arc guide rail 9, as indicated by H1 of FIG. 2. A rack and pinion method and a belt method can be employed.

The above-mentioned three-axis drive (G1, H1) enables the X-ray head 10 to carry out the isocentric motion (the X-ray head 10 is oriented toward the isocenter 5a) on the quarter sphere with the isocenter 5a as the center. Moreover, the above-mentioned two-axis drive (R1, R2) enables the X-ray head 10 to carry out the pseudo non-isocentric motion (the X-ray head 10 is oriented toward a desirable point within a three-dimensional region 5b (refer to FIG. 2) near the periphery of the isocenter 5a) on the quarter sphere. This pseudo non-isocentric operation is the head swinging motion around the inertia center of the X-ray head 10, thus, the especially quick motion can be carried out as compared with the isocentric operation. The quickly pursuing motion with pseudo non-isocentric and quick response property enables the collimation of the head to pursue even the quick motion of, for example, a cardiac beat at a quick response and precise manner.

The microwave generating unit 70 includes a klystron and has a circulator 21 related to a waveguide and a dummy load 22, and sends a microwave for electron acceleration through the driven type waveguide system 11 to the X-ray head 10. Here, it sends the microwave of a C band (5.6 GHz).

The driven type waveguide system 11 is the waveguide to send the microwave generated by the microwave generating unit 70 to the X-ray head 10. It links (couples) a joint 14a, a link arm 12, a joint 14b, a link arm 13, a joint 14c, a link arm 15, a joint 16 and the X-ray head 10 to one another to thereby form the linking (coupling) mechanism. Only the joint 14a can be rotated around the axis in the Y-axis direction. The joint 14b, the joint 14c and the joint 16 can be rotated around the axis in the X-axis direction. Incidentally, the X-ray head 10 at the link (couple) tip is slid along the arc guide rail 9 by the circulation moving mechanism 68, and is swung around the joint 16 by the first head swing mechanism 131.

Then, the joints 14a, 14b, 14c and 16 contain a rotary RF coupler 50 (described later) for transmitting the microwave through an axis rotation. The link arms 12, 13 and 15 contain a waveguide 51 (described later), and they are electromagnetically connected through the joints 14a to 14c and 16. The microwave generated by the microwave generating unit 70 is sent through the joint 14a, the link arm 12, the joint 14b, the link arm 13, the joint 14c, the link arm 15 and the joint 16 to the X-ray head 10.

The real time imager 30 is the X-ray CT inspecting unit. The X-ray CT inspecting unit continuously irradiates diagnosis X-rays 3b, which are weak fan X-ray beams, to the treatment field 5 of the subject 4, from many directions over the entire circumference of 360 degrees, and detects its transmission image, and then performs an imaging process on the detected data, and thereby displays a three-dimensional tomographic diagnosis image of the treatment field 5 on a computer screen. The real time imager 30 is controlled by the system control unit 80.

The typical X-ray CT inspecting unit can be used as the real time imager 30. The real time imager 30 is held at the posture tilted at a preset angle (for example, a slant of 20 to 30 degrees for the vertical axis) by an imager tilting mechanism 20 shown in FIG. 1. When the imager tilting mechanism 20 is driven, the real time imager 30 is tilted around the axis (indicated by K1 in FIG. 1) so that an irradiation angle of the diagnosis X-ray 3b can be changed. Incidentally, the real time imager 30 and the arc guide rail 9 are mechanically rigidly coupled and have the common coordinate as the standard.

The real time imager 30 is controlled such that the arc guide rail 9 and the X-ray head 10 do not interfere with each other. If the typical X-ray camera is used as the imager, as necessary, the small gold plate is embedded in the vicinity of the irradiation field and marks the irradiation field as a standard.

A doughnut vacuum bath having a central opening as a diagnosis space is included, and the patient 4, together with the treatment bed 7-2, as the subject is inserted into and withdrawn from this diagnosis space. The inside of the vacuum bath is exhausted and evacuated by a vacuum pump through an exhausting port (not shown).

A plurality of diagnosis X-ray generating units arranged on a concentric circle near an outer circumference and a plurality of sensor arrays concentrically arranged near an inner circumference correspondingly to them are placed inside the vacuum bath, respectively. The diagnosis X-ray generating units and the sensor arrays are shifted and arranged in the X-axis direction so that the diagnosis X-rays 3b are irradiated in the shape of a fan in a direction tilted forwardly for a radius of the vacuum bath. Thus, the diagnosis X-rays 3b in the shape of the fan are not shielded by the sensor arrays on the X-ray irradiation side (the upper side), and they can be transmitted through the subject 4 in the diagnosing space and detected by the sensor arrays on the opposite side (the lower side).

Moreover, a beam limiter, an electron gun driving circuit, an image signal digitizer and the like are respectively placed at the proper positions in the vacuum bath. The diagnosis X-rays 3b in the shape of the fan emitted from the diagnosis X-ray generating unit are throttled by a collimator (not shown) and further limited to a width at an irradiation position by the beam limiter and transmitted through the subject 4 and then detected by the sensor arrays.

The sensor arrays receive (detect) the diagnosis X-rays 3b transmitted through the subject 4. They are densely arranged and fixed on the circumference surrounding the diagnosis space in which the subject 4 is placed, and have a large number of ultra high sensitivity CdTe sensors, and have a resolution of 0.5 mm. Width of taking an image of one shot at a time of an inspection is 80 mm. Also, an irradiation time of the diagnosis X-rays 3b is 0.0025 to 0.01 seconds per shot.

The X-ray transmission data detected by the sensor arrays is converted into an electric signal proportional to the transmission X-ray dose, and sent through a pre-amplifier and a main amplifier to an image signal digitizer and a data recorder, and then recorded as a diagnosis image data. The photographing through the diagnosis X-rays 3b, the data recording and the like are controlled by the system control unit 80. The recorded diagnosis image data is outputted from the data recorder to an imager signal processing unit 31 (refer to FIG. 9) and processed by the imager signal processing unit 31. The processed data is displayed as the X-ray CT diagnosis image of the affected part 5 on the display of the system control unit 80.

An anode, a cathode and a grid electrode of a gate array inside the diagnosis X-ray generating unit and a power supply are respectively connected to the output side of the X-ray generation control unit of the real time imager 30. When the system control unit 80 outputs an X-ray generation instruction signal to the X-ray generation control unit, the X-ray generation control unit controls the power supplying operation to the electron gun driving circuit of the power supply, in accordance with the instruction, and selects the grid electrode from the gate array suitable for taking the image of the part. In response to it, the electron ray is emitted from any of the cathodes inside the diagnosis X-ray generating unit. Then, a minus bias voltage applied to the selected grid electrode is released, and it becomes at a zero potential. The electron ray is passed through a hole of the grid electrode and inputted to the anode. When the electron ray is inputted to the anode, a secondary X-ray is generated from the anode, and the diagnosis X-rays 3b in the shape of the fan are emitted through a collimator attached to a window to the patient 4.

The real time imager 30 needs not be the X-ray CT inspecting unit. This may be a set of the X-ray source and the sensor array opposite thereto. It is shown in FIG. 23.

Figure 23:
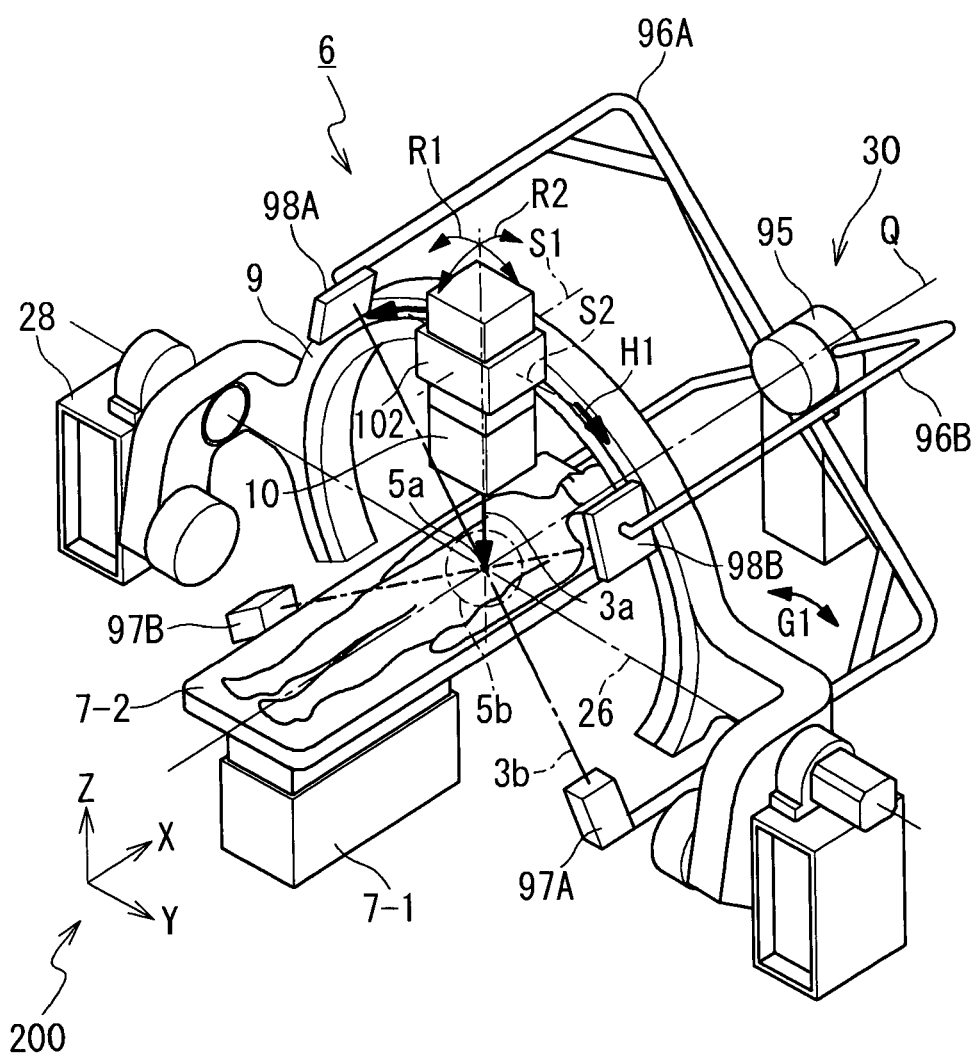
FIG. 23 is a perspective view showing another embodiment in the first embodiment of the radiotherapy apparatus of the present invention.

FIG. 23 is a perspective view showing another configuration of the first embodiment in the radiotherapy apparatus of the present invention. FIG. 23 differs from FIGS. 1 to 3 in the configuration of the real time imager 30.

This real time imager 30 has a rotation driving mechanism 95, retaining frames 96A, 96B, two sets of X-ray source 97A or 97B and sensor array 98A or 98B constituting the typical X-ray camera.

The retaining frames 96A, 96B, respectively, includes the X-ray sources 97A, 97B placed at one ends thereof, and the sensor arrays 98A, 98B placed at the other ends constituting the typical X-ray camera. The centers of the retaining frames 96A, 96B are installed to the rotation driving mechanism 95.

The sensor array 98A is placed near one side in the Y-axis direction of the X-ray head 10. The perpendicular from the center of the flat surface on the sensor side is oriented toward the isocenter 5a, and the X-ray source 97A is placed on that extension line. Similarly, the sensor array 98B is placed near the other side in the Y-axis direction of the X-ray head 10. The perpendicular from the center of the flat surface on the sensor side is oriented toward the isocenter 5a, and the X-ray source 97B is placed on that extension line.

The rotation driving mechanism 95 rotates the retaining frames 96A, 96B with a real time imager rotation axis Q, which passes through the isocenter 5a and is parallel to the X-axis, as a center, in such a way that the two sets of the X-ray sources 97A, 97B and the set of the sensor arrays 98A, 98B are located at the desirable positions.

The two sets of the X-ray source 97A or 97B and the sensor array 98A or 98B are controlled so as to be held at preset angles between one another. The preset angles are 60 degrees to 20 degrees of the sensor array 98A or the sensor array 98B, the isocenter 5a and the X-ray head 10. Preferably, they are 45 degrees to 30 degrees. They are set in accordance with the condition that the X-ray head 10 and the X-ray sources 97A, 97B do not have influence on one another and they are accurately operated and the diagnosis image having the sufficient precision can be obtained.

However, as for two sets of X-ray source 97A or 97B and sensor array 98A or 98B, if the visual lines of the sets of the X-ray source and the sensor array are not coincident with each other, the positional controls may be carried out independently of each other.

In the case of FIG. 23, the anodes, the cathodes and the grid electrodes inside the X-ray sources 97A, 97B, and the power supply are respectively connected to the output side of the X-ray generation control unit of the real time imager 30. When the system control unit 80 outputs the X-ray generation instruction signal to the X-ray generation control unit, the X-ray generation control unit controls the power supplying operation of the power supply to the electron gun driving circuit, in accordance with the instruction, and operates the rotation driving mechanism 95 to thereby move the two sets of the X-ray source and the sensor array to the optimal positions on the basis of the positional relation to the X-ray head 10. In response to the movements, the electron ray is emitted from the cathodes inside the X-ray sources 97A, 97B. Then, the minus bias voltage applied to the grid electrode is released, and it becomes at the zero potential. The electron ray is passed through the hole of the grid electrode and inputted to the anode. When the electron ray is inputted to the anode, the secondary X-ray is generated from the anode, and the diagnosis X-rays 3b in the shape of the fan are emitted through the collimator attached to the window to the patient 4.

The X-ray sources 97A, 97B are surely located oppositely to each other, with the straight line through which the isocenter 5a and the X-ray head 10 in FIG. 23 are connected between. The sensor arrays 98A, 98B are similarly located. Consequently, the motions at the respective parts inside the body of the patient 4 can be grasped quickly and accurately.

Also, the sensor arrays 98A, 98B are installed on the side of the X-ray head 10. Thus, the treatment X-rays 3a that are very strong X-rays are never inputted to the sensor arrays 98A, 98B.

The SAD (Source Axis Distance) shown in FIG. 1 corresponds to the distance from the isocenter 5a to a target 121 (described later) inside the X-ray head 10. In this embodiment, the SAD serving as the standard is set to 80 to 100 cm.

Next, the X-ray head 10 will be described below in detail with reference to FIGS. 4, 5.

FIG. 4A is an entire view showing the configuration of the X-ray head 10 applied to the radiotherapy apparatus of the present invention, FIG. 4B is a sectional view taking on the line A—A of FIG. 4A, and FIG. 4C is a sectional view taking on the line B—B of FIG. 4A.

The X-ray head 10 has the small electron linac for generating the treatment X-ray 3a having an electron energy between 4 MeV and 10 MeV. This is movably supported by the arc guide rail 9 so that the radiation can be irradiated from the many directions by the three-dimensional movement within the range of the quarter sphere on the upper half with the isocenter 5a as the center. Together with it, this is linked (coupled) to the rotary RF coupler 16 of the driven type waveguide system 11 under the condition that can be swung.

In the X-ray head 10, the main body of the X-ray head 10 is covered by a head cover 101, and an output unit 120 for emitting the radiation is installed on the tip side of the main body. An electric circuit/cool water circuit 116, an accelerating structure 110, an RF window 52, the waveguide 51, a part 50B of the rotary RF coupler, an exhaust tube 107, an ion pump 112 a target exhaust room 119, the target 121 and a cold plate 122 are installed inside the head cover 101 for covering the head main body.

A cable (not shown) connected to an external power source from an insulation glass 103 of a tail of the accelerating structure 110 is inserted into the head cover 101, and connected to a cathode 105 of an electron gun 104. An anode 106 is placed opposite to this cathode 105. The power supply of the electron gun 104 is controlled by the system control unit 80.

The portion between the cathode 105 and the anode 106 is exhausted through the exhaust tube 107 linked (coupled) to the ion pump 112. The space to be exhausted is linked (coupled) from the electron gun 104 to the accelerating structure 110 and further linked (coupled) from the accelerating structure 110 to the output unit 120. Since the ion pump 112 is directly linked (coupled) to the accelerating structure 110, the degree of vacuum of the accelerating structure 110 can be always kept high vacuum, and the stable electron rays can be stably accelerated. Consequently, the treatment X-ray 3a can be stably outputted.

The length from the insulation glass 103 to the tip of the accelerating structure 110 is about 360 mm. This scale is miniaturized very much to about ⅓ that of the conventional accelerating structure and its weight is made lighter. This is because the microwave of the C band (5.6 GHz) of the high frequency (the high energy) is used instead of the microwave of the S band that has been conventionally used.

Figure 5:
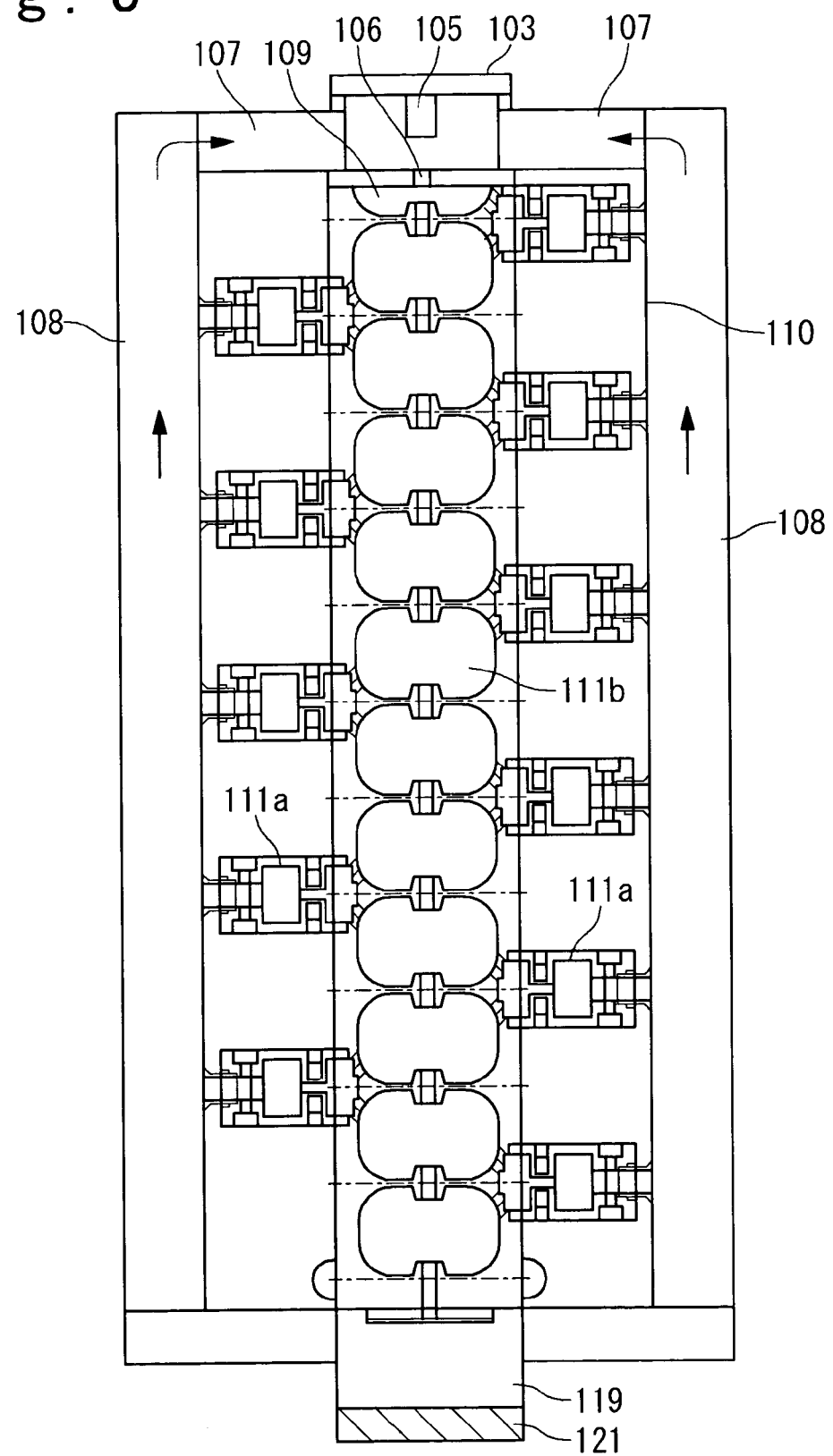
FIG. 5 is an enlarged view in the vicinity of an electron gun and an accelerating structure of FIG. 4C.

FIG. 5 is the enlarged view showing the vicinity of the electron gun 104 of FIG. 4C and the accelerating structure 110.

As shown in FIG. 5, the central hole of the anode 106 of the electron gun 104 is linked (coupled) to a buncher cavity 109 of the accelerating structure 110. A plurality of acceleration cavities 111b having central holes for electron beam passage are further jointly formed inside the accelerating structure 110. The accelerating structure 110 accelerates the electron rays outputted from the electron gun 104 while passing through the central holes of the plurality of acceleration cavities 111b and the buncher cavity 109, and crashes into the X-ray target 121, as the electron beam of the high energy. The acceleration cavities 111b are respectively linked (coupled) through side couple cavities 111a to a pair of right and left side exhaust tubes 108. The pair of right and left side exhaust tubes 108 is connected through the exhaust tube 107 to the ion pump 112 and exhausted and evacuated thereby. That is, the accelerating structure 110 is exhausted through the side exhaust tube 108 and evacuated by the ion pump 112.

The waveguide 51 is linked (coupled) to the accelerating structure 110. The waveguide 51 is linked (coupled) through the RF window 52 made of ceramic and rotary RF couplers 50A, 50B (—the driven waveguide system 11—) to the microwave generating unit 70. The RF window 52 is the inlet to prevent the leakage of $SF_6$ gas sealed in the waveguide 51 and also guide the microwave into the accelerating structure 110. The microwave generating unit 70 use the klystron type that is excellent in output stability. A power supply circuit of the microwave generating unit 70 is connected to the system control unit 80.

The output unit 120 is placed at the tip of the main body of the X-ray head 10 covered with the head cover 101. It includes the X-ray target 121, a target cooling plate 122, a first collimator 123 and a flattening filter 124. They are arranged in series along the optical axis of the electron beam, from the electron gun 104 through the accelerating structure 110 to the flattening filter 124. Then, the accelerated electron ray is passed through a target exhaust room 119 and inputted to the target 121 of the output unit 120.

The target 121 emits a braking radiation X-ray in accordance with the input of the acceleration electron of the high energy. The target cooling plate 122 is installed so as not to receive the thermal damage caused by the heat generated at the time of the emission of the braking X-ray. A single high melting point metal, such as tungsten, tantalum, and the like, or an alloy composed of them is used for the target 121.

The first collimator 123 is made of a material, such as tungsten, which has the excellent shielding property against the radiation and has little generation of thermal neutrons. The X-rays from the target 121 are throttled to a preset beam width and guided to the flattening filter 124.

The flattening filter 124 averages the strengths of the X-rays emitted from the target 121, and makes into the treatment X-ray 3a having a uniform dose distribution.

Moreover, a secondary collimator 125 and an ionization box 126 for measuring a dose are installed on the tip side of the output unit 120. The secondary collimator 125 is made of the material having the high shielding property through which the treatment X-rays 3a can not be transmitted, such as tungsten and the like. The treatment X-rays 3a in which the X-rays from the flattening filter 124 are throttled to the preset beam width are guided to the ionization box 126. This secondary collimator 125 is detachably threaded into the end side of the first collimator 123.

The ionization box 126 measures the dose of the passed X-rays. It is installed at the tip of the secondary collimator 125, and gas having preset components is sealed therein. A detecting circuit (not shown) for detecting discharged charges is connected thereto. This detecting circuit is connected to the input side of the system control unit 80. The system control unit 80 calculates the dose of the X-rays emitted from the X-ray head 10, in accordance with the input signal from the ionization box 126 for measuring the dose, and stores in a memory, as the dose data for the treatment received by the patient 4.

In the radiotherapy apparatus 6 of the present invention, the X-ray head 10 is small such that the total length is 500 to 600 mm, the width is 500 mm and the depth is 300 mm. Moreover, its weight is made light, such as 60 to 80 kg. However, it can generate the treatment X-rays having the electron energy between 4 MeV and 10 MeV, which is the high energy. This reason is as follows. Since the microwave of the C band (5.6 GHz) of the high frequency (the high energy) is used, the accelerating structure 110 is small and light. Since the accelerating structure 110 is small, a deviating magnet for deviating the electron rays and the apparatuses related thereto are not required. And, the apparatus for generating the microwave (the microwave generating unit 70) is placed outside the X-ray head 10. That is, since the entire weight is lightened and the entire scale is miniaturized, the X-ray head 10 can be moved to the desirable position quickly and rapidly at the small force.

Also, it can be further miniaturized and lightened by using an accelerating structure that can accelerate by means of a microwave of an X band of a higher frequency. In that case, it can be attained by changing the designs of the various units (for example, changing the dimensions of the respective configurations in the driven waveguide system 11 and the dimension of the acceleration cavity 111b in the accelerating structure 110 and the like while matching to the frequency of the microwave).

The apparatus in this embodiment can irradiate the radiation from the quarter sphere on the upper half portion. However, the radiation can be further irradiated from the entire upper half ball by further miniaturizing a precise inspection unit of a non-magnetic type and making into a unit so as to contain this on the side of the treatment irradiation head.

The head swing mechanism of the two axes of the X-ray head 10 will be described below in detail with reference to FIGS. 6 to 8.

Figure 6:
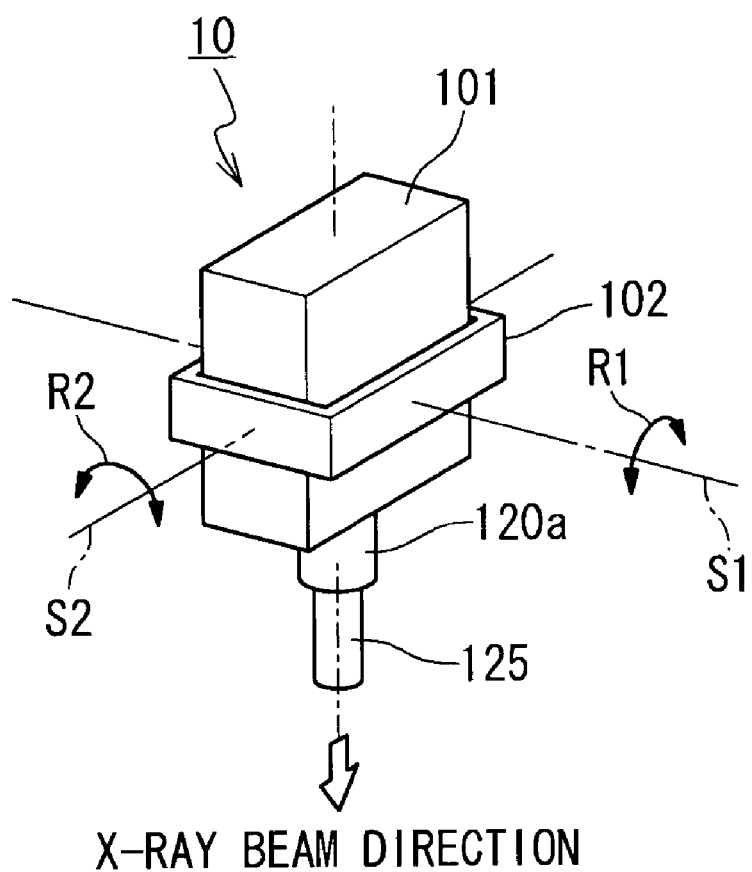
FIG. 6 is a perspective view showing an X-ray head supported by a support frame.

FIG. 6 is a perspective view showing the X-ray head 10 supported by the support frame 102.

As shown in FIG. 6, the head cover 101 of the X-ray head 10 is supported by the support frame 102 having gimbal structure. The support frame 102 is installed to the position of the coordinate which includes the inertia center of the X-ray head 10 and through which the first swing axis S1 and the second swing axis S2 pass. Then, it is swung as indicated by R1 around the first swing axis S1 by the first head swing mechanism 131. Similarly, it is swung as indicated by R2 around the second swing axis S2, by the second head swing mechanism 132.

Figure 7A:
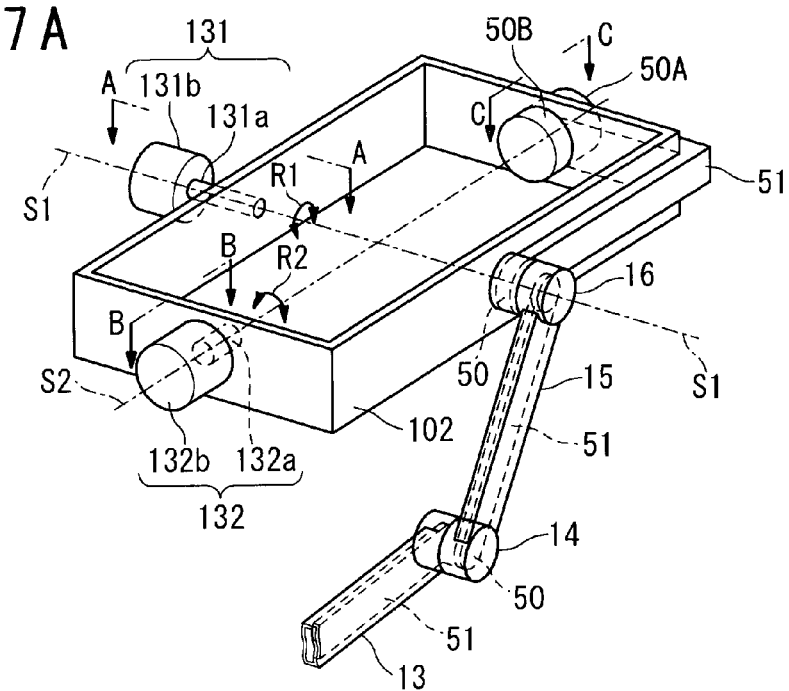
FIG. 7A is a view showing an entire configuration of a two-axis head swing mechanism of a support frame.
Figure 7B:
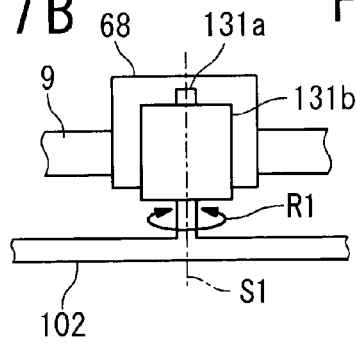
FIG. 7B is a view showing a servomotor for driving an S1 head swing in FIG. 7A.
Figure 7C:
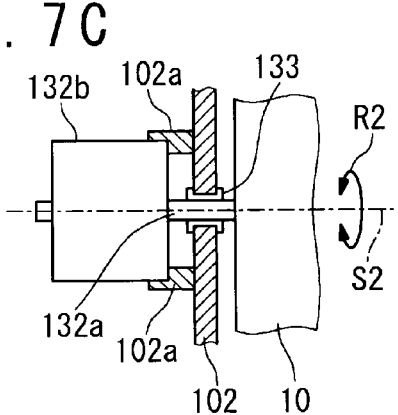
FIG. 7C is a view showing a servomotor for driving an S2 head swing in FIG. 7A.
Figure 7D:
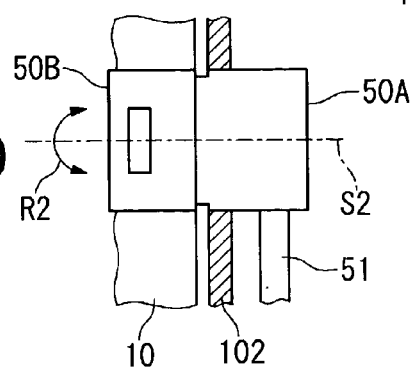
FIG. 7D is a view showing a pair of rotary RF couplers in FIG. 7A.

FIGS. 7A to 7D are the views the configuration of the two-axis head swing mechanism of the support frame. FIG. 7A shows the entire configuration, FIG. 7B shows an S1 swing driving servomotor 131b, FIG. 7C shows an S2 head swing driving servomotor 132b, and FIG. 7D shows a pair of rotary RF couplers 50A, 50B.

As shown in FIG. 7A, the rotary RF coupler 16 of the driven waveguide system 11 and the S1 swing driving servomotor 131b are respectively installed onto two sides of the support frame 102, which are opposite to each other, along the first swing axis S1. Similarly, the pair of rotary RF couplers 50A, 50B and the S2 head swing driving servomotor 132b are respectively installed onto two sides, which are different from the above-mentioned two sides and opposite to each other, along the second swing axis S2.

As shown in FIGS. 7A, 7B, the rotary RF coupler 16 of the driven waveguide system 11 is installed to the center of the longer side on the one side of the support frame 102. In such a way that a driving shaft 131a of the S1 swing driving servomotor 131b faces on the coupler 16, the driving shaft 131a is installed to the center of the opposite long side of the support frame 102 so as to overlap with the first swing axis 1. Then, the S1 swing driving servomotor 131b is fixed to and supported by the head circulation moving mechanism 68 on the arc guide rail 9. When the servomotor driving shaft 131a is rotationally driven, the X-ray head 10 is swung around the first swing axis S1, as indicated by R1.

As shown in FIGS. 7A, 7C and 7D, the pair of rotary RF couplers 50A, 50B are installed to the center of the shorter side on the one side of the support frame 102. In such a way that a driving shaft 132a of the S2 head swing driving servomotor 132b faces on the pair of rotary RF couplers 50A, 50B, the driving shaft 132a is installed to the center of the opposite short side of the frame 102 so as to overlap with the second swing axis S2. Then, the main body of the S2 head swing driving servomotor 132b is fixed to and supported by a bracket 102a on the support frame side, and the driving shaft 132a is rotatably supported through a bearing 133 by the support frame 102. When the servomotor driving shaft 132a is rotationally driven, as shown in FIG. 7C, the X-ray head 10 is swung around the S2 driving axis.

As shown in FIGS. 7A, 7D, the waveguides 51 are placed inside the respective link arms 13, 15 of the driven waveguide system 11, and the rotary RF couplers 50 are placed inside the respective joints 14, 16. Moreover, the microwaves are guided through the pair of rotary RF couplers 50A, 50B into the accelerating structure 110 inside the X-ray head 10.

The rotary RF coupler serving as the joint of the waveguide to transmit the microwaves will be described below with reference to FIGS. 8 to 10B.

Figure 8:
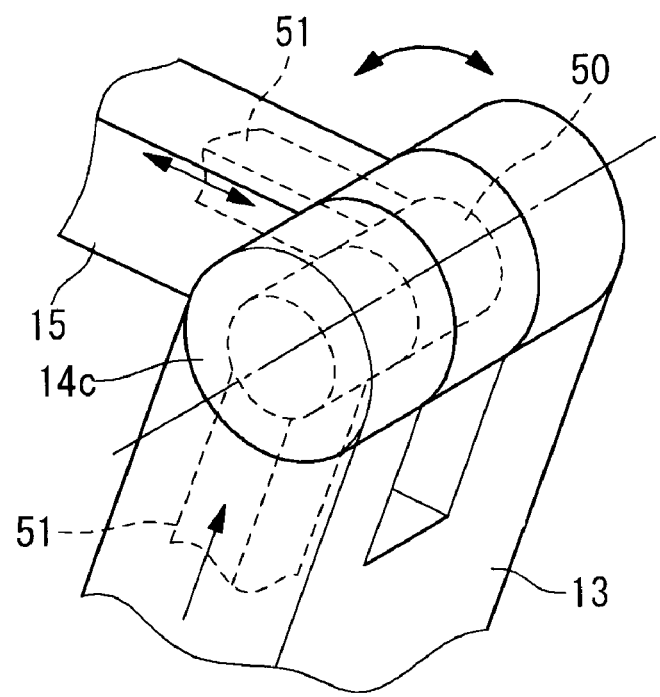
FIG. 8 is a view showing a configuration of a joint having therein a rotary RF coupler.

FIG. 8 is a view showing the configuration of the joint including therein the rotary RF coupler 50. FIG. 8 shows a joint 14c as a representation. However, a joint 14a, a joint 14b, a joint 16, and the pair of rotary RF couplers 50A, 50B are similarly configured.

As shown in FIG. 8, the waveguides 51 are placed inside the link arms 13, 15. The waveguides 51 are electromagnetically connected through the rotary RF couplers 50 inside the joints 14a to 14c and 16.

Figure 9:
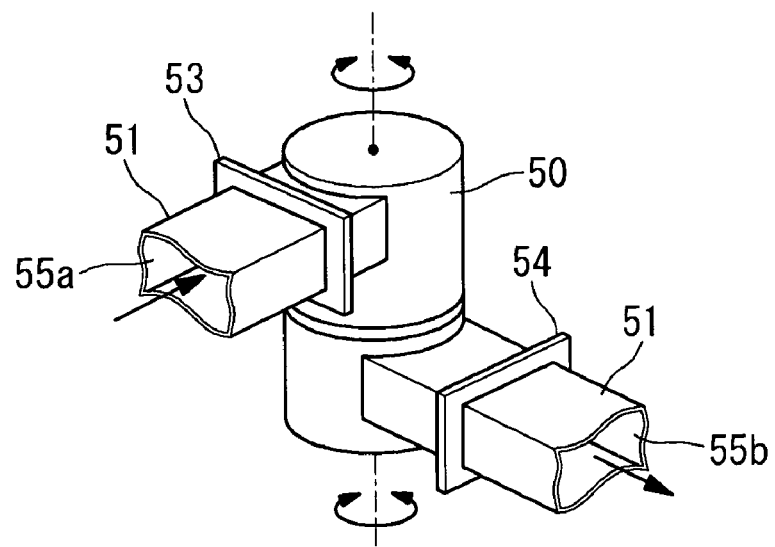
FIG. 9 is a perspective view showing in detail the configuration of the rotary RF coupler shown in FIG. 8.

FIG. 9 is a perspective view showing in detail the configuration of the rotary RF coupler 50 shown in FIG. 8.

As shown in FIG. 9, the rotary RF couplers 50 are connected through flange joints 53, 54 to the respective waveguides 51. Then, the rotary RF coupler 50 transmits the microwave for acceleration of a waveguide 55a to a waveguide 55b through shaft rotation.

Figures 10A, 10B:
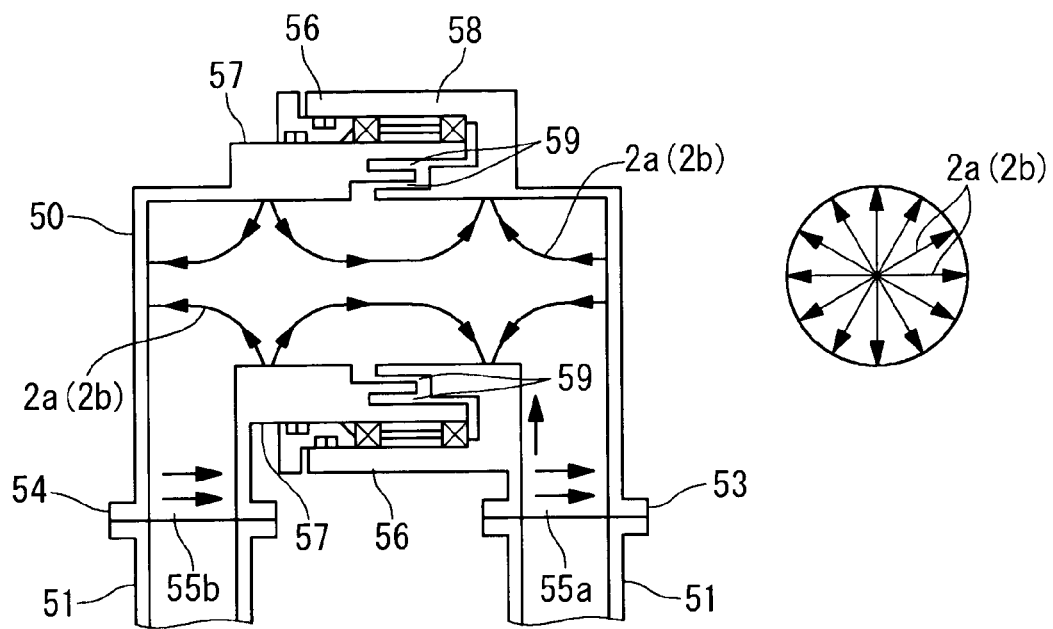
FIG. 10A is a sectional view showing in detail the rotary RF coupler of FIG. 9.
FIG. 10B shows an example of a mode of a microwave inside the rotary RF coupler.

FIG. 10A is a sectional view showing in detail the rotary RF coupler 50 of FIG. 9. And, FIG. 10B shows an example of a mode of the microwave inside the rotary RF coupler 50.

As shown in FIG. 10A, the waveguides 55a, 55b of the waveguide 51 are linked (coupled) to the rotational space surrounded with rotational members 56, 57, a bearing 58 and a λ/4 wavelength choke 59 inside the rotary RF coupler 50. The microwave is guided through it at an in-tube mode (an electric force line 2a (2b)) exemplified in FIG. 10B. Due to the combination of the rotary RF couplers 50 and the waveguide 51 as mentioned above, the microwave generating unit 70, such as a klystron and the like, fixed on the ground can smoothly send the microwave for the acceleration to the moving X-ray head 10.

A control system in the embodiment of the radiotherapy apparatus of the present invention will be described below.

Figure 11:
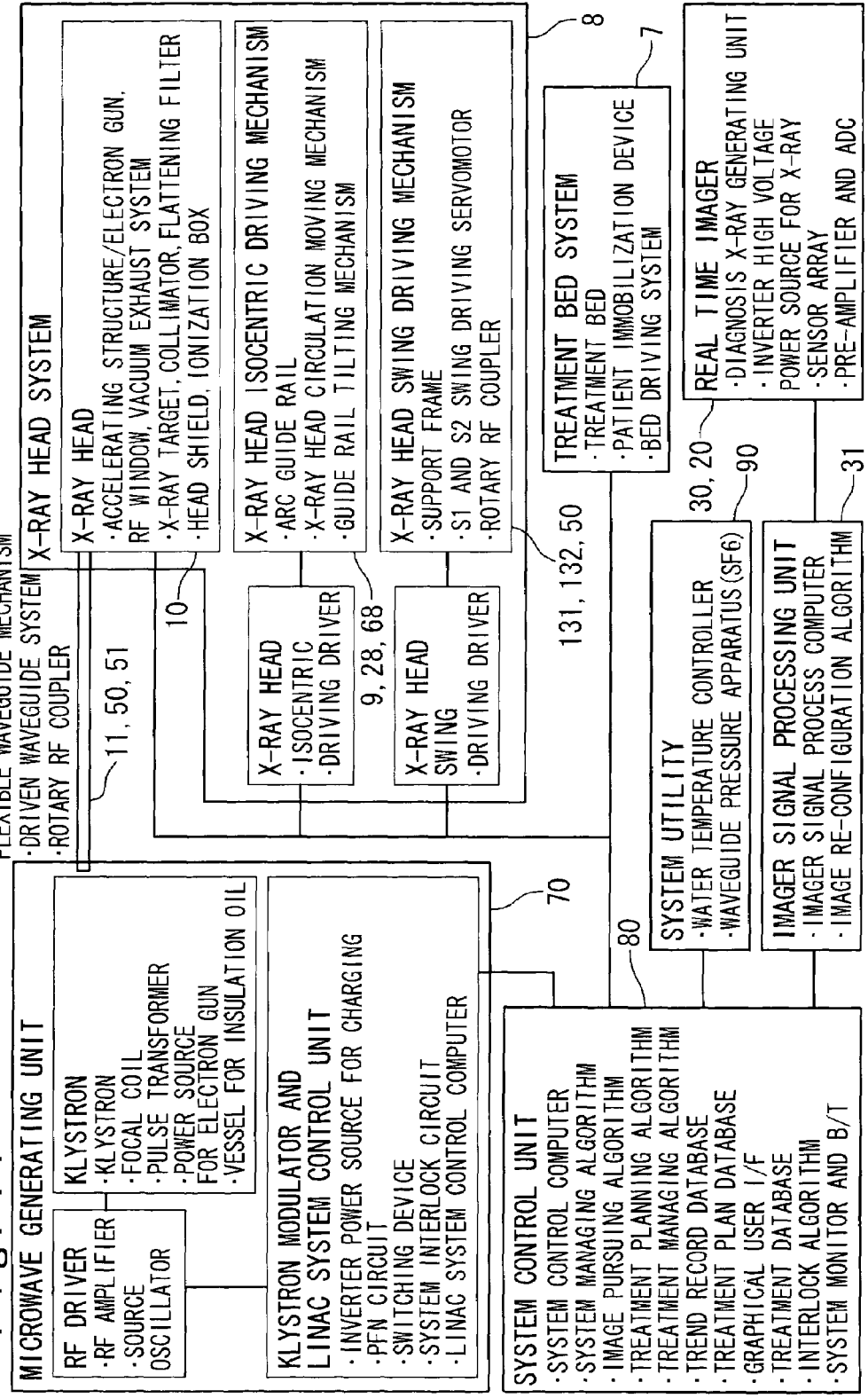
FIG. 11 is a block diagram showing a control system of the embodiment of the radiotherapy apparatus of the present invention.

FIG. 11 is a block diagram showing the control system in the embodiment of the radiotherapy apparatus of the present invention. The control system in this embodiment includes the treatment bed system 7, the X-ray head system 8, the real time imager 30, the imager signal processing unit 31, the microwave generating unit 70, the system control unit 80 and a system utility 90. This substantially has the system configuration in which the system control unit 80 manages and controls the entire configuration.

The system control unit 80 has a system control computer and includes, as a computer program, a system managing algorithm, an image pursuing algorithm, a treatment planning algorithm, a treatment managing algorithm, a graphical user interface (GUI) and an interlock algorithm and contains a treatment plan database, a trend record database and a treatment plan database. Also, this includes a system monitor (a display) and BIT. With this as a center, other system blocks are connected respectively to thereby exchange an input output signal.

The treatment plan database stores therein a treatment plan data as a data related to a treatment plan planned by a doctor. The treatment plan data is based on various inspections carried out before an operation. The treatment plan data relates a patient attribute data, a patient image data, an absorption dose data, a treatment dose data, an affected part position data and the like to one another.

Here, the patient attribute data indicates the name of the patient 4, the data of birth and the like. The patient image data indicates an X-ray tomographic diagnosis image of the patient 4. The absorption dose data relates to the setting data of the absorption dose which includes an absorption dose of the radiation (the X-rays) to the affected part 5, its irradiating method (the number, the absorption dose of one trial, the irradiation direction (route) and the like). The treatment dose data relates to the setting data of the treatment dose which includes a treatment dose of the radiation (the X-rays) to the affected part 5, its irradiating method (the number, the treatment dose of one trial, the irradiation direction (route) and the like). The affected part position data relates to the position of the affected part 5. The position of the affected part 5 may be the definition region 5-1 which will be described later.

The trend record database stores therein an irradiation result data related to actual results of an irradiation treatment. The irradiation result data relates to the actually irradiated radiation (X-rays) at a time of a treatment. The irradiation result data relates the patient attribute data, a totaled treatment dose, a totaled absorption dose, a treatment dose for each irradiation direction (each portal number), an estimated absorption amount, a target coordinate (a coordinate of an irradiation target at the affected part 5) and a mechanical coordinate (a coordinate of an irradiation field 5' which is actually irradiated) and the like to one another.

The treatment database relates a kind of a substance, a radiation absorption amount curve indicative of a relation between a thickness of a substance and an absorption amount of radiation (X-rays) and the like to one another, and stores therein.

The system managing algorithm manages and controls the entire system control unit 80 such as the respective algorithms, the GUI, the system monitor (the display) and the BIT and the like.

The treatment planning algorithm calculates the treatment dose data (the treatment dose of the X-rays for each irradiation direction (each route) and the totaled treatment dose) and the like, in accordance with the treatment plan database (the X-ray tomographic diagnosis image of the patient 4 and the absorption dose data) and the treatment database (the radiation absorption amount curve for each substance)). Then, they are indicated on the display to receive the confirmation of a doctor. As necessary, the doctor changes the irradiation direction, the absorption dose of the X-rays and the like so that it becomes the desirable treatment dose data. After the confirmation of the doctor, they are stored in the treatment plan database.

The treatment managing algorithm controls the X-ray head system 8 so that the X-ray head 10 is oriented toward a preset direction, in accordance with the treatment plan data from the treatment plan database and/or the head swing amount of the X-ray head 10 from the image pursuing algorithm.

Also, it stores the irradiation result data obtained from the imager signal processing unit 31, the X-ray head system 8, the image pursuing algorithm and the like during the treatment, in the trend record database.

The image pursuing algorithm calculates the coordinate of the affected part 5 in accordance with the image data for the pursuit obtained from the imager signal processing unit 31. Also, it determines the coordinate of the irradiation field 5' of the X-ray head 10 in accordance with the various data obtained from the X-ray head system 8. Then, it calculates the head swing amount of the X-ray head 10, in accordance with the coordinate of the affected part 5 and the coordinate of the irradiation field 5'.

The interlock algorithm stops the treatment X-ray 3a and the diagnosis X-ray 3b if the preset conditions are satisfied. As the preset conditions, there are a case that an emergent stop button is pushed, a case that the irradiation field 5' and the affected part 5 are separated by a preset distance or more, a case that at least one of the treatment dose to the patient 4 and the absorption dose exceeds a preset allowable value to each of them, a case that the diagnosis X-ray 3b is stopped when the treatment X-ray 3a is irradiated, a case that the treatment X-ray 3a is stopped when the diagnosis X-ray 3b is irradiated, and other cases.

The X-ray transmission data detected by the real time imager 30 is re-configured to the diagnosis image by an image reconfiguration algorithm in the imager signal processing unit 31 and transmitted to the system control unit 80. Consequently, the image diagnosis is generated at real time during the treatment. The doctor can carry out the treatment while observing the diagnosis image displayed on a computer display.

The microwave generating unit 70 includes a klystron modulator and linac system control unit, a klystron and an RF driver. The klystron is connected through the driven waveguide system 11 to the X-ray head 10, and this serves as a supply source for sending a microwave to the accelerating structure 110.

The X-ray head system 8 includes the X-ray head 10, the isocentric driving mechanism (including the arc guide rail 9, the guide rail tilting mechanism 28 and the head circulation moving mechanism 68) and the swing driving mechanism (including the first head swing mechanism 131, the second head swing mechanism 132 and the rotary RF coupler 50). The isocentric driving mechanism and the swing driving mechanism are connected through the respective drivers corresponding to the respective mechanisms (an isocentric driving driver and a head swing driving driver) to the system control unit 80 to thereby control the two-axis head swing drives of the head circulation moving mechanism 68 of the X-ray head 10 at the time of the isocentric irradiation and the X-ray head 10 at the time of the pseudo isocentric irradiation, respectively.

The operation of the first embodiment in the radiotherapy apparatus of the present invention will be described below with reference to the attached drawings.

At first, the positional calibration in the operation of the first embodiment in the radiotherapy apparatus of the present invention is explained.

Figure 12A:
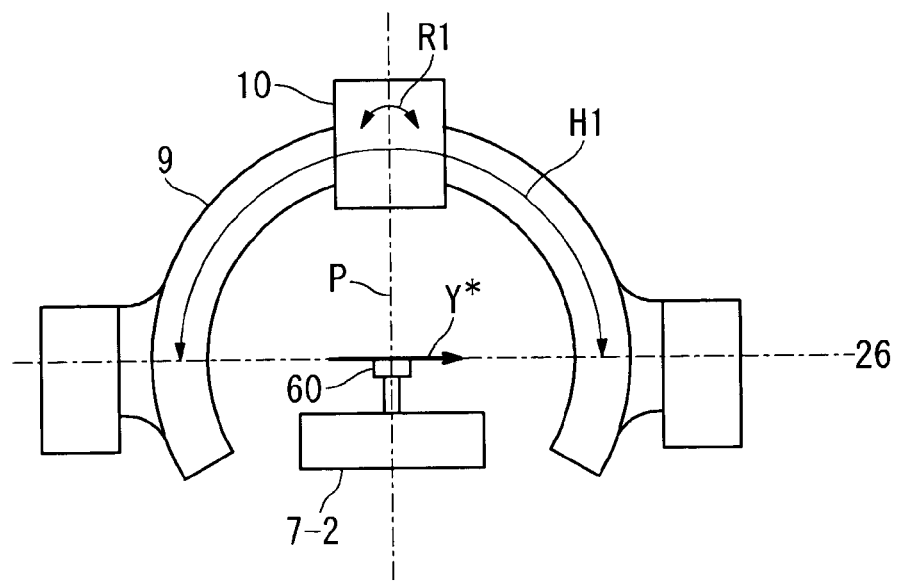
FIG. 12A is a front view explaining a positional calibration of the radiotherapy apparatus.
Figure 12B:
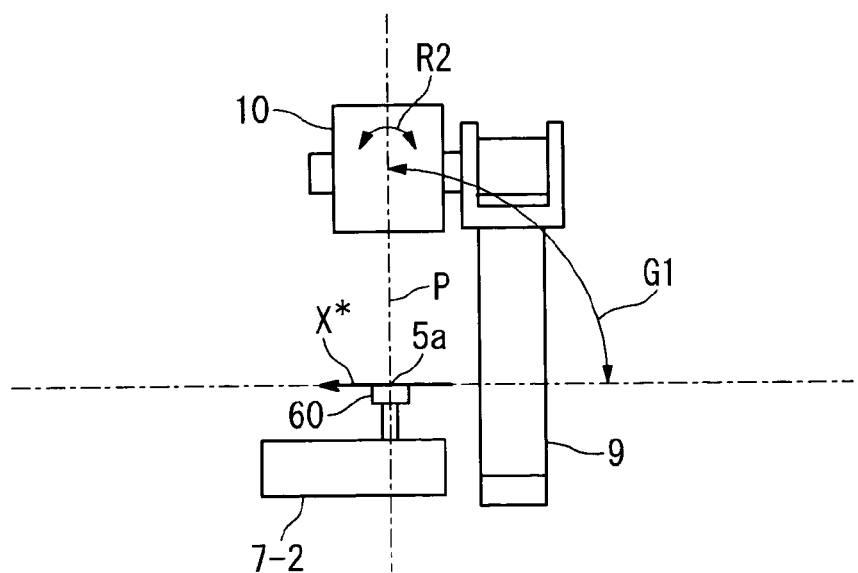
FIG. 12B is a side view explaining the positional calibration of the radiotherapy apparatus.

FIGS. 12A and 12B are views explaining the positional calibration of the radiotherapy apparatus 6. FIG. 12A shows a front view, and FIG. 12B shows a side view. In addition to the configurations (their explanations are omitted) shown in FIGS. 1 to 3, a CCD camera 60 is placed on the treatment bed 7-2.

The CCD camera 60 is placed such that a center of that light receiving surface overlaps with the isocenter 5a and the light receiving surface is horizontal. The CCD camera 60 is connected to a laser magnitude analyzer (not shown).

In the X-ray head 10, a laser transmitter (not shown) (for example, a small type He—Ne laser of a low output and the like) is arranged such that it is coaxial to the emitted X-ray.

The position calibrating method is explained.

(1) Step S1-1

At the state of FIGS. 12A, 12B, the laser transmitter of the X-ray head 10 outputs a laser to the CCD camera 60.

(2) Step S1-2

The CCD camera 60 receives the laser, and outputs the result of the light receptions to the laser magnitude analyzer (not shown).

(3) Step S1-3

The laser magnitude analyzer (not shown) detects the magnitude distribution of the laser, and calculates the deviations (the X-axis direction, the Y-axis direction and the Z-axis direction) between the isocenter 5a (=the center of the light receiving surface of the CCD camera 60) and the peak position of the laser magnitudes.

(4) Step S1-4

The calculated deviations are stored, as correction values, in the memory (not shown) of the system control unit 80.

Due to the above-mentioned position calibrating method, the positional deviation caused by the distortion at the time of production, the bending resulting from its self-weight, the stress at the time of the installation and the like in the large mechanical member such as the arc guide rail 9 can precisely be corrected in a short time by using a very easy method.

Thus, the positional precision can be improved. In the case of this embodiment, the positional resolution can be reduced to about 20 m.

Such a positional calibration is performed when the radiotherapy apparatus 6 is installed and when a periodical maintenance is carried out. However, it may be done for each preset number of usages and for each radiation treatment.

The temporal timing for each operation in the operations of the embodiment in the radiotherapy apparatus of the present invention will be described below.

FIGS. 13A to 13C are timing charts in the operations of the embodiment in the radiotherapy apparatus of the present invention. FIG. 13A shows the timings of the operations when the diagnosis image is processed, FIG. 13B shows the timings of the head swing operations of the X-ray head 10 and the image pursuing calculation based on the diagnosis image processed, and FIG. 13C shows the timings of the irradiation of the treatment X-ray, respectively.

(0) Before Time t0

At first, when a main switch of the radiotherapy apparatus 6 is turned ON, the power supplies of the treatment bed system 7, the X-ray head system 8, the real time imager 30, the microwave generating unit 70, the system control unit 80 and the system utility 90 become at waiting states, respectively. In such a way that the treatment bed system 7 is actuated to thereby move the patient 4 together with the treatment bed 7-2 into a treatment area and that the real time imager 30 is actuated to thereby make the affected part 5 coincide with the isocenter 5a of the apparatus, the positional adjustment is carried out by moving the treatment bed 7-2. After the completion of this isocentric position adjustment, the real time image diagnosis of the real time imager 30 and the radiotherapy of the X-ray head 10 are started.

(1) Step S2-1: Time Between t0 and t1

Typically, the X-ray camera (the real time imager 30) irradiates the diagnosis X-ray 3b from the diagnosis X-ray generating unit to the irradiation field 5'. Then, the sensor arrays detect the X-ray transmission data as the diagnosis image data. In order to minimize the exposure, the irradiation time of the diagnosis X-ray 3b is limited to t0 to t1.

(2) Step S2-2: Time Between t1 and t2

The detected diagnosis image data is converted into a current signal proportional to the transmission X-ray amount and captured through the preamplifier and the main amplifier by the image signal digitizer and the data recorder.

(3) Step S2-3: Time Between t2 and t3

The recorded diagnosis image data is outputted from the data recorder to the imager signal processing unit 31. Then, it is operationally processed by using the image re-configuration algorithm of the imager signal processing unit 31 and converted into a pursuit image data. The pursuit image data is the data indicative of the diagnosis images at respective coordinate points (Xi, Yi, Zi), (i=1 to n:n is the number of the data) in the coordinate system of the radiotherapy apparatus 6. The pursuit image data is outputted to the system control unit 80.

The pursuit image data is reproduced and indicated as the (X-ray CT) diagnosis image of the affected part 5 on the display of the system control unit 80.

The real time imager 30 and the imager signal processing unit 31 again repeat the processes at the time between t0 and t3 after the time t3. In FIGS. 13A to 13C, the processes at the time between t0 and t3 are equal to the processes at the time between t10 and t13 and the time between t20 and t23 and the like.

In such a way that a direct ray, a leakage ray and a scattered ray of the treatment X-ray 3a do not have any influence on the sensor arrays (the detectors) of the real time imager 30, the X-ray head 10 is interlocked such that the treatment X-ray 3a is not irradiated at least between the times t0 and t1 while the diagnosis X-rays 3b are irradiated.

The total time between t0 and t3 necessary for those diagnosis image processes (the steps S2-1 to S2-3) is 0.01 seconds. That is, one cycle time of the diagnosis image process is 0.01 seconds. This is the sample rate enough to pursue the quick motion of the cardiac beat or the like.

(4) Step S2-4: Time Between t3 and t4

The image pursuing algorithm of the system control unit 80 is used to carry out the following image pursuing calculation.

On the basis of the pursuit image data, the coordinate of the affected part 5 is extracted (a coordinate point (X, Y, Z) in the coordinate system of the radiotherapy apparatus 6). On the other hand, the current coordinate of the irradiation field 5' in the X-ray head 10 (the coordinate point (x, y, z) in the coordinate system of the radiotherapy apparatus 6) is calculated on the basis of the positions (the coordinates) of the guide rail tilting mechanism 28, the head circulation moving mechanism 68, the first head swing mechanism 131 and the second head swing mechanism 132, and the rotational angle and the like. Then, (1) if a distance L between the two points=|(X, Y, Z)−(x, y, z)| is a preset value $L_{02}$ or less, the head swing is not carried out, and (2) if the distance L is a preset value $L_{01}$ or more, a head swing amount is assumed to be $_0$, and if the $L_{02}$<the distance L<the $L_{01}$, head swing amounts (1, 2) of the X-ray head 10 are calculated on the basis of the coordinate of the affected part 5 and the coordinate of the irradiation field 5'. The head swing amount $_0$ is the angle when it is oriented toward the direction of the coordinate of the affected part 5, for example, by an angle corresponding to the distance $L_{01}$.

However, the head swing amounts (1, 2) of the X-ray head 10 are a micro deviation angle (a head swing angle) 1 (the rotational direction and the value of the rotational angle) around the S1 head swing driving axis and a micro deviation angle (a head swing angle) 2 (the rotational direction and the value of the rotational angle) around the S2 head swing driving axis.

The $L_{01}$ is the maximum length at which the X-ray head 10 can be swung between the times t4 and t5. Also, the $L_{02}$ is the value of the error estimated when the coordinate point (X, Y, Z) of the affected part 5 and the coordinate point (x, y, z) of the irradiation field 5' are calculated.

The state (the coordinate point (X, Y, Z)) of the movement (the motion) of this affected part 5 is indicated on the display of the system control unit 80. However, not only the affected part 5 but also the peripheral region (for example, the contour line 5-2 (described later) containing the affected part 5) may be similarly indicated.

(5) Step S2-5: Time Between t4 and t5

On the basis of the calculated head swing amounts (1, 2) of the X-ray head 10, in accordance with the treatment managing algorithm of the system control unit 80, a head swing driving signal indicative of the head swing amounts (1, 2) of the X-ray head 10 is outputted to the X-ray head system 8.

The first head swing mechanism 131 and the second head swing mechanism 132 are driven by the X-ray head swing driving driver of the X-ray head system 8, in accordance with the head swing driving signal. Consequently, the X-ray head 10 is oriented toward the desirable direction.

The system control unit 80 again repeats the processes at the time between t3 and t5, from the time t13 after the time t5. In FIGS. 13A to 13C, the processes at the time between t3 and t5 are equal to the processes at the time between t13 and t15 and the time between t23 and t25 and so on.

The total time between t3 to t5 necessary for the image pursuing calculation and the X-ray head swing operation (the steps S2-4 to S2-5) is 0.01 seconds. That is, one cycle time of the image pursuing calculation and the X-ray head swing operation is 0.01 seconds. This is the rate enough to pursue the quick motion such as the cardiac beat.

At the time between t4 and t5 while the S1 swing driving servomotor 131b of the first head swing mechanism 131 and the S2 head swing driving servomotor 132b of the second head swing mechanism 132 are driven, there may be the possibility of the erroneous operation of the head swing angle. Thus, in such a way that the treatment X-ray 3a is not irradiated, the X-ray head 10 is interlocked to thereby secure the safety.

(6) Step S2-6: Time Between t5 and t6

The system managing algorithm of the system control unit 80 is used to output the treatment X-ray irradiation signal, as the signal for indicating the irradiation of the treatment X-rays 3a at the time t5, to the X-ray head 10. The interlock of the X-ray head 10 is released to start irradiating the treatment X-rays 3a to the affected part 5. The irradiation time between t5 and t6 of the treatment X-rays 3a is 0.0025 to 0.01 seconds. The duty of the irradiation is about 50%.

The system control unit 80 again repeats the processes at the time between t5 and t6, from the time t15 after the time t6. In FIGS. 13A to 13C, the processes at the time between t5 and t6 are equal to the processes at the time between t15 and t16 and the time between t25 and t26.

The total of the times t5 to t6 necessary for this treatment X-ray irradiation (the step S2-6) is 0.01 seconds. That is, one cycle time of the treatment X-ray irradiation is 0.01 seconds. This is the rate enough to pursue the quick motion of the cardiac beat or the like.

Here, the manner when the treatment X-rays 3a are irradiated while the X-ray head 10 is swung is further described with reference to the drawings.

Figure 14:
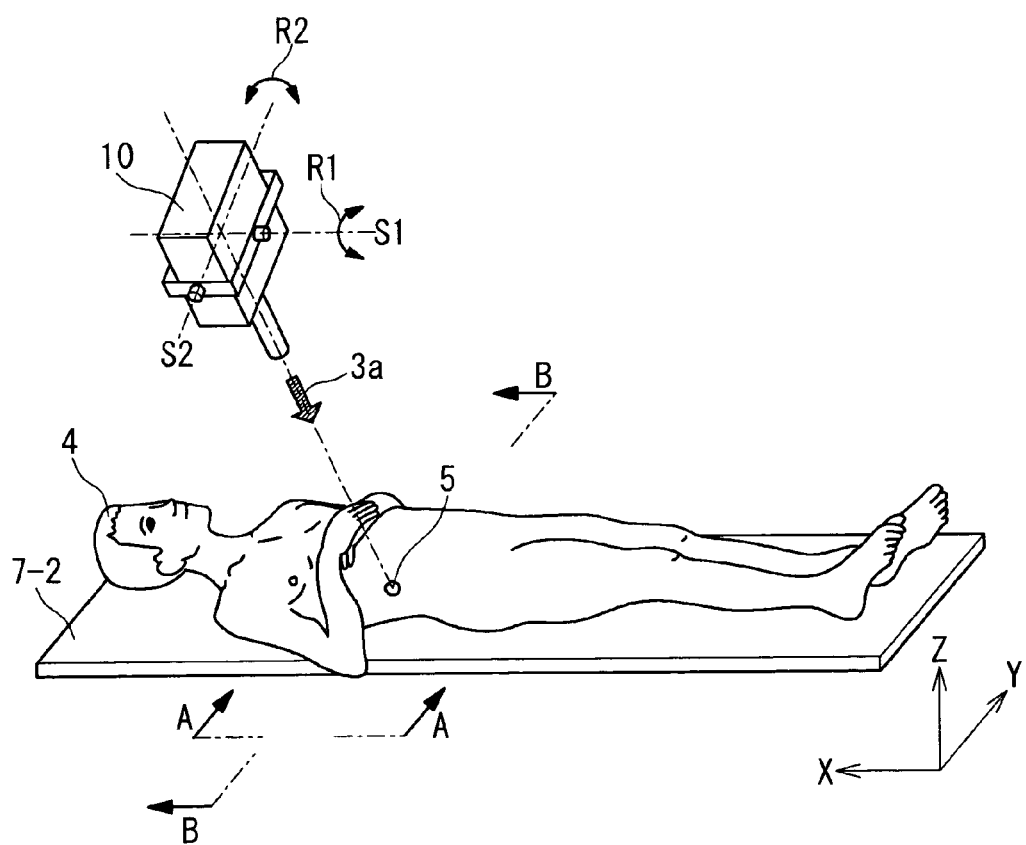
FIG. 14 is a perspective view showing a manner of radiotherapy through an X-ray head.

FIG. 14 is a perspective view showing the manner of the radiotherapy using the X-ray head 10. The X-ray head 10 irradiates the X-rays to the affected part 5.

Figure 15:
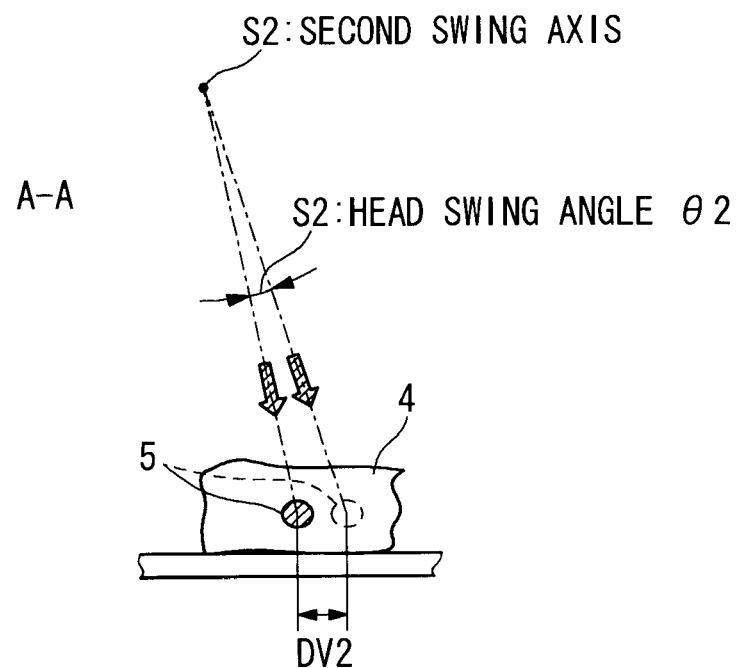
FIG. 15 is a view explaining a manner of irradiating a treatment X-ray while swinging the X-ray head and shows an A—A section in FIG. 14.
Figure 16:
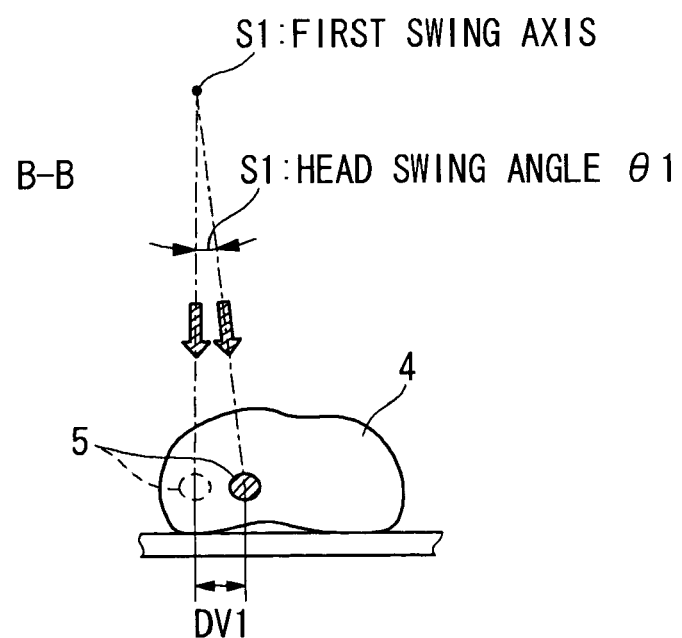
FIG. 16 is a view explaining a manner of irradiating a treatment X-ray while swinging the X-ray head and shows a B—B section in FIG. 14.

FIGS. 15, 16 are views showing the manner when the treatment X-rays 3a are irradiated while the X-ray head 10 is swung. FIG. 15 shows the A—A section in FIG. 14, and FIG. 16 shows the B—B section in FIG. 14.

In order to irradiate while pursuing the movement of the irradiation field, the system control unit 80 calculates shift amounts DV1, DV2 from the irradiation field 5' of the affected part 5 in the X-axis direction and the Y-axis direction, in accordance with the current coordinate (x, y, z) of the irradiation field 5' of the X-ray head 10 and the calculated position (the coordinate (X, Y, Z)) of the affected part 5, at the above-mentioned times t3 to t4. Then, in accordance with the shift amounts DV1, DV2, a preset calculation equation is used to determine the deviation angles 1, 2 caused by the movements around the first swing axis S1 and the second swing axis S2, respectively.

At the above-mentioned times t5 to t6, the X-ray head 10 is swung by the deviation angles 1 around the first swing axis S1 and swung by the deviation angles 2 around the second swing axis S2. Then, simultaneously with the stop of the head swing, the treatment X-rays 3a are emitted from the X-ray head 10.

Due to the above-mentioned steps S2-1 to S2-6, the radiation (the X-rays) can be irradiated at the high precision to the affected part 5, such as the tumor, which is moved by the influence of the motion and the condition of the organs, such as the breath and the cardiac beat, the peristalsis, the urine amount within the urinary bladder and the like below the chin, since the collimation of the X-ray head 10 pursues quickly at the high correspondence. That is, within 0.03 seconds including the processing time of the diagnosis image, the head swing operation of the X-ray head 10 can be carried out and the radiation (the X-rays) can be irradiated, which can quickly pursue the motion of the irradiation field (the affected part).

In the above-mentioned processes, at the step S2-4 (the time between t3 and t4) the angle when the neck of the X-ray head 10 is swung at the step S2-5 is limited to a preset value. This reason is as follows. As the head swing angle becomes larger, the time necessary for the head swing becomes longer. Meanwhile, the affected part 5 is further moved. Thus, the coordinate point (x, y, z) of the irradiation field 5' in the X-ray head 10 is largely deviated from the position of the coordinate point (X, Y, Z) in the affected part 5.

The fast motion of the affected part 5 to be pursued by the X-ray head 10 is caused by the breath and the cardiac beat. In this case, the affected part 5 is moving within the substantially same region (however, the route is not always same). Thus, even once the coordinate point (x, y, z) of the irradiation field 5' in the X-ray head 10 and the coordinate point (X, Y, Z) of the affected part 5 are not perfectly coincident with each other, they can be coincident after that.

If an abnormality is brought about in the obtainment of the diagnosis image data and/or the image pursuit calculation, at that point, the irradiation of the treatment X-rays 3a is interlocked to thereby stop the irradiation, and the safety is secured. This apparatus is designed so as to irradiate the treatment X-rays 3a after confirming the normal executions of the head swing of the X-ray head 10 and the positioning operation.

Then, if the deviation between the coordinate point (x, y, z) of the irradiation field 5' and the coordinate point (X, Y, Z) of the affected part 5 is equal to or greater than a preset value, the irradiation of the treatment X-rays 3a at the step S2-6 (the time between t5 and t6) is not carried out in that cycle.

Also, as necessary, the system control unit 80 can move the head circulation moving mechanism 68, the tilting mechanism 28 and the treatment bed system 7 to thereby match the collimation of the X-ray head 10 with the affected part 5.

That is, the system control unit 80 calculates the head swing amount (for the first head swing mechanism 131 and the second head swing mechanism 132) of the X-ray head 10 and the movement amount (for the head circulation moving mechanism 68, the tilting mechanism 28 and the treatment bed system 7), in accordance with the coordinate of the affected part 5 and the coordinate of the irradiation field 5', at the time between t3 and t4. Next, at the time between t4 and t5, it outputs the head swing amount of the X-ray head 10 and the movement amount to the X-ray head system 8. Then, it moves the first head swing mechanism 131, the second head swing mechanism 132, the head circulation moving mechanism 68, the tilting mechanism 28 and the treatment bed system 7 to thereby match the collimation of the X-ray head 10 with the affected part 5.

Before the start of the irradiation to the treatment X-rays 3a, the irradiation of the diagnosing beam 3b is started at the timing t10. The operational flow proceeds to the next diagnosis image processing cycles t10 to t13. Next, at the timing t5 after the irradiation of the diagnosing beam 3b, the interlock of the X-ray head 10 is released to then resume the irradiation of the treatment beam 3a.

As mentioned above, the cycle having the total of 0.03 seconds (T0) is repeated which is composed of: the diagnosis image processing cycle (in FIGS. 13A to 13C, 0 to Ta) of 0.01 seconds; the image pursuit calculating cycle and the X-ray head swing cycle (in FIGS. 13A to 13C, Ta to Tb) of 0.01 seconds; and the treatment X-ray irradiating cycle (in FIGS. 13A to 13C, Tb to Tc) of 0.01 seconds. That is, the radiation irradiating head can be accurately oriented toward the irradiation target for each approximately 1/30 seconds. Even if the affected part (the irradiation field) has the fastest motion such as the cardiac beat, the irradiation target can be accurately pursued at real time, and the radiation can be irradiated.

The procedure of the pseudo non-isocentric treatment will be described below.

FIGS. 17A to 17F are flowcharts showing the procedure of the pseudo non-isocentric treatment by using the indication on the display.

(1) Step S3-1

In the case of the radiotherapy, the doctor plans a treatment schedule. The treatment schedule is based on the various inspections performed prior to the operation. The treatment schedule is stored in the treatment planning database.

Moreover, the doctor can carry out the radiotherapy at the high precision and at the high sureness by using the radiotherapy apparatus of the present invention during the operation and diagnosing the image of the focus of the patient directly at the real time.

(2) Step S3-2

As shown in FIG. 17A, by using the real time imager 30 and the imager signal processing unit 31, the diagnosis image of the affected part 5 and the region near it is re-configured and reproduced and indicated on the display of the system control unit 80.

The re-configuration is carried out at the above-mentioned steps S2-1 to S2-3. However, at this stage, the steps S2-4 to S2-6 are not carried out.

(3) Step S3-3

As shown in FIG. 17B, the doctor confirms respective sectional views of the affected part 5 on the display and defines the contour line of the irradiation field 5' for the image pursuit. Here, prior to the start of the treatment, the mapping of the irradiation field 5' is already ended (the treatment planning database), and the contour of the irradiation field 5' is defined at a plurality of slices with reference to it. The region defined by the contour is the definition region 5-1. The definition region 5-1 includes the affected part 5. The definition region 5-1 is stored in the treatment plan database.

The treatment planning algorithm calculates the treatment dose data (the treatment dose of the X-rays for each irradiation direction (route) and the totaled treatment dose) and the like, in accordance with the treatment plan database (including the definition region 5-1) and the treatment database. Then, it is indicated on the display to receive the confirmation of the doctor. As necessary, the doctor changes the irradiation direction, the absorption dose of the X-rays and the like so that it becomes the desirable treatment dose data. After the confirmation of the doctor, the treatment dose data is stored in the treatment plan database.

(4) Step S3-4

As shown in FIG. 17C, the image contour is extracted by the image pursuing algorithm of the system control unit 80. That is, the pattern matching between the diagnosis image of the actual affected part 5 and the contour line of the defined definition region 5-1 is carried out to indicate as the contour line 5-2 (described later). Then, the image pursuit is started. The doctor visually confirms the situation of the image pursuit.

The image pursuit is carried out at the above-mentioned steps S2-4. Thus, the above-mentioned steps S2-1 to S2-4 are repeatedly performed. However, at this stage, the steps S2-5 to S2-6 are not performed.

(5) Step S3-5

As shown in FIG. 17D, after the image pursuit becomes stable, the doctor operates a master arm switch and sets the X-ray head system 8 to an ARMED state. The X-ray head system 8 indicates, on the display, the collimation with a cross hair line and the irradiation volume with a red color. Then, the pursuit (the head swing) of the X-ray head 10 is carried out simultaneously with the image pursuit. Since the pursuits of the image and the X-ray head 10 are continued, the collimation and the irradiation volume are automatically followed in association with the movement of the irradiation field 5'.

The pursuit (the head swing) of the X-ray head 10 is carried out at the step S2-5. Thus, the steps S2-1 to S2-5 are repeatedly performed. However, at this stage, the treatment X-ray 3a is not emitted. Hence, the step S2-6 is not performed.

(6) Step S3-6

As shown in FIG. 17E, the triggering operation carried out by the doctor starts irradiating the treatment X-rays 3a. The scheduled irradiation time is already determined at the stage of the treatment plan. A count-down is started on the display. On the other hand, the irradiation time (Step S2-6: Time between t5 and t6) of one irradiation is already determined. Thus, the count is reduced during the repetition of the irradiation in the short time (the time between t5 and t6) Then, when it becomes finally zero, the treatment X-ray 3a is automatically stopped. The treatment dose of the treatment X-rays 3a is detected by the ionization box 126 and outputted to the treatment managing algorithm.

The irradiation of the treatment X-rays 3a is carried out at the step S2-6. Thus, the steps S2-1 to S2-6 are repeatedly performed.

Also, in accordance with the treatment managing algorithm, (all or a part of) the irradiation result data obtained from the imager signal processing unit 31, the X-ray head system 8, the image pursuing algorithm and the like during the treatment is continuously indicated on the display. The doctor, while confirming (all or a part of) this irradiation result data, continues to trigger and irradiate. The irradiation result data is stored in the trend record database.

The system control unit 80 continues to alternately sample (pursue) the diagnosis image and irradiate the treatment X-rays 3a at a high speed, and continues to pursue the image and irradiate the treatment X-rays at real time. Even before the count-down becomes zero, if the doctor releases the triggering, the treatment X-ray 3a is stopped immediately at that timing. Thus, the safety can be sufficiently secured.

(7) Step S3-7

As shown in FIG. 17F, the doctor sets the master arm switch at a SAFE position, sets the system at a safe state, and moves the X-ray head 10 to a next irradiation position.

At this stage, the steps S2-1 to S2-3 are done. The steps S2-4 to S2-6 are not done.

The doctor, after the irradiation at the respective portals are ended and the series of the irradiation are ended, confirms the total dose that is the total of the accumulated exposure doses. That is, in accordance with the treatment managing algorithm, the data is read out from the trend record database, and the accumulated dose and the accumulated dose distribution within one cycle are indicated on the screen. The data related to the treatment is stored in a treatment file (including the irradiation result data) prepared for each patient 4 within the trend record database.

Here, the method of carrying out the pattern matching between the actual diagnosis image of the affected part 5 at the step S3-4 and the contour line of the definition region 5-1 is further explained.

FIGS. 18A to 18E are views showing the relation among the affected part 5, the definition region 5-1 and the contour line 5-2 resulting from the pattern-matching. FIG. 18A shows the relation between the affected part 5 and the definition region 5-1, and FIGS. 18B to 18E show the relation between the affected part 5 and the contour line 5-2.

(1) Step S4-1

As shown in FIG. 18A, the doctor indicates the definition region 5-1 on the display in the manner of a drawing tool, by using a touch pen that can be drawn on the display or a pointer such as a mouse.

(2) Step S4-2

The treatment planning algorithm extracts the diagnosis image in the definition region 5-1 in accordance with the definition region 5-1 drawn on the display and the diagnosis image on the display. Then, it grasps the shape, the coordinate and the brightness distribution of the diagnosis image. Or, it extracts the shape in the brightness range occupying a preset rate (for example, 90%) of the definition region 5-1 shown in FIG. 18B and thereby grasps the shape, the coordinate and the brightness distribution of the diagnosis image.

(3) Step S4-3

The treatment planning algorithm determines the center of gravity, for the shape of the range of the definition region 5-1 or the shape of the brightness range indicative of the preset rate. Then, it indicates on the display by means of [+]. For example, the center of gravity of the definition region 5-1 (FIG. 18A) is as shown in FIG. 18C. The center of the gravity of the brightness range (FIG. 18B) indicative of the preset rate is as shown in FIG. 18D. Incidentally, only the center of the definition region 5-1 may be merely indicated, as shown in FIG. 18E.

As mentioned above, the pattern matching is ended.

It is possible to carry out a binary value indication, in which the range of the definition region 5-1 or the brightness range indicative of the preset rate is indicated on the display by using a particular color, and the others are indicated by using the different colors. It is possible to easily judge the definition region 5-1.

Here, the brightness distribution is grasped as follows.

Figure 19:
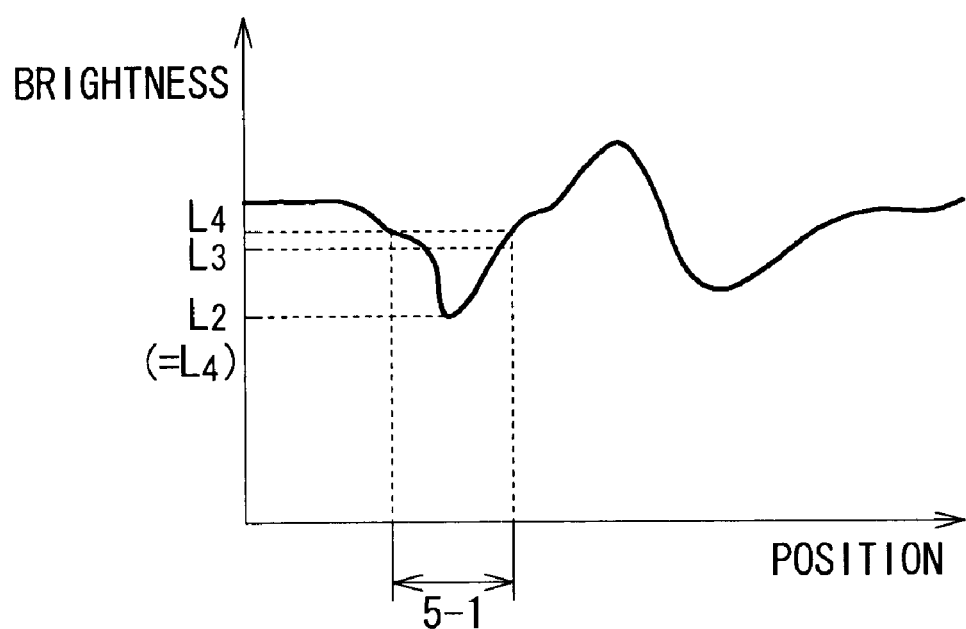
FIG. 19 is a graph showing an example of a brightness distribution in the diagnosis image.

FIG. 19 is a graph showing one example of the brightness distribution in the diagnosis image. The vertical axis represents the brightness, and the horizontal axis represents the position of the diagnosis image.

It is understood that the brightness in the definition region 5-1 of the diagnosis image is in a range between L4 and L2, from the graph. Thus, the brightness range of the definition region 5-1 is between L4 and L2.

Also, the brightness range occupying the preset range (for example, 90%) in the definition region 5-1 is the continuous brightness range between L3 and L2, which is selected so as to occupy the area of the preset range (for example, 90%) in the definition region 5-1, in the brightness range between L4 and L2.

A different position indicative of the same brightness is separated from the definition region 5-1. Thus, it is not recognized.

According to the treating apparatus in this embodiment, the high-speed head swing operation can be performed on the radiation irradiating head (the X-ray head 10) within 0.02 seconds, including the imaging process, and it can follow the motion of the irradiation field (the affected part). Thus, the radiation can be irradiated at the high precision (the irradiation time of 0.01 seconds). In this way, correspondingly to the motion of the affected part, the non-isocentric irradiation can be carried out at the high correspondence and at the high precision. Thus, the portion, in which the irradiation target of the tumor or the like is moved by the influence of the motion and the condition of the organs, such as the breath and the cardiac beat, the peristalsis, the urine amount within the urinary bladder and the like below the chin, can be set to the treatment target.

This embodiment has been explained by exemplifying the combination of the radiotherapy apparatus and the real time imager 30 as the inspecting unit. However, the present invention is not limited thereto A different non-magnetic inspecting unit, such as the typical X-ray camera, PET (Positron Emission Tomography) in a special field and the like can be combined with the radiotherapy apparatus.

The typical X-ray camera needs two or more cameras having different visual lines. Also, a soft tissue whose contrast is low and the like can not be imaged. Thus, a landmark whose contrast is high, such as an osseous tissue and the like, is used as a standard so that the irradiation field can be positioned in advance through the X-ray CT, MRI and the like. Or, a small gold marker or the like is embedded in the vicinity of the irradiation field and used as the marker. Or, the idea is tried such that the image can be emphasized by using a differential imaging process and a contrast medium such as DSA (Digital Subtraction Angiography). Also, in the X-ray CT and PET, a real time image reconfiguration calculation of a high speed is carried out for real time imaging.

SECOND EMBODIMENT

A second embodiment in the radiotherapy apparatus of the present invention will be described below with reference to FIGS. 20, 21. In this embodiment, the explanations of the portions overlapping with those in the first embodiment are omitted.

Figure 20:
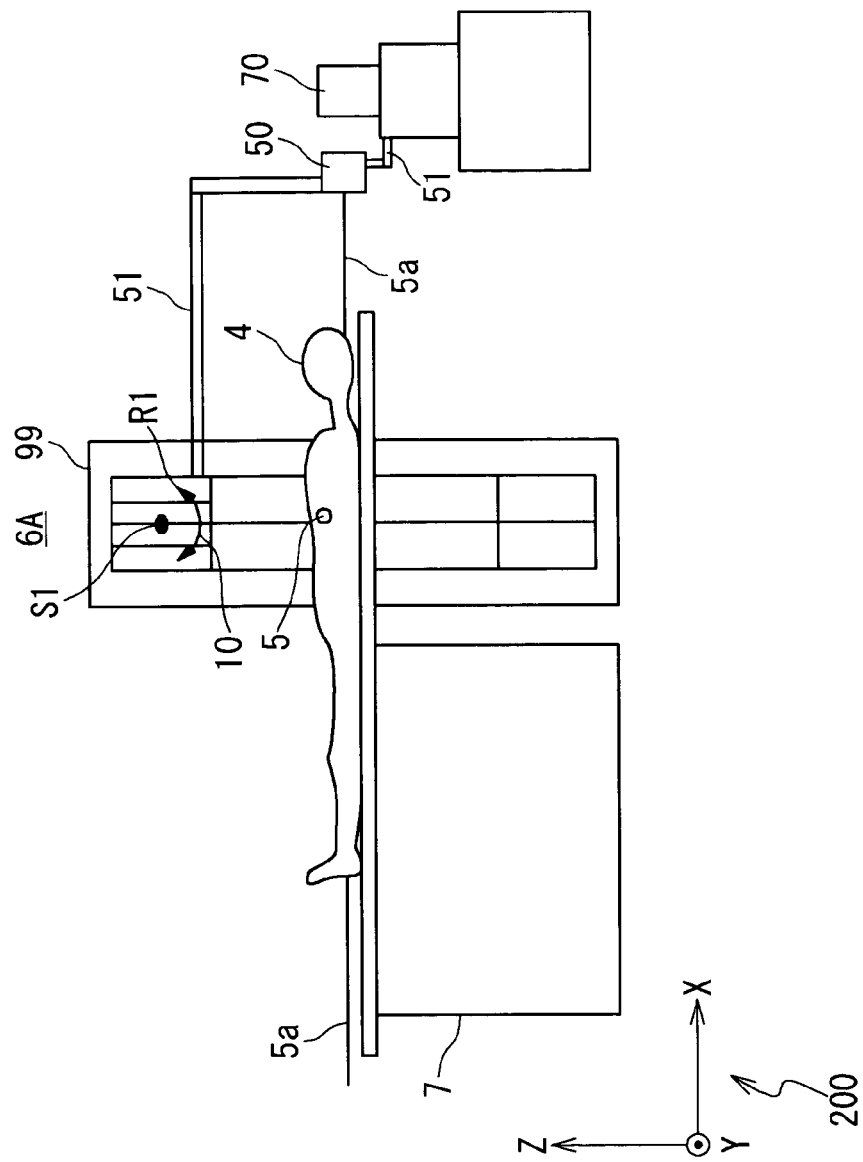
FIG. 20 is a side view showing a configuration in a second embodiment of the radiotherapy apparatus of the present invention.
Figure 21:
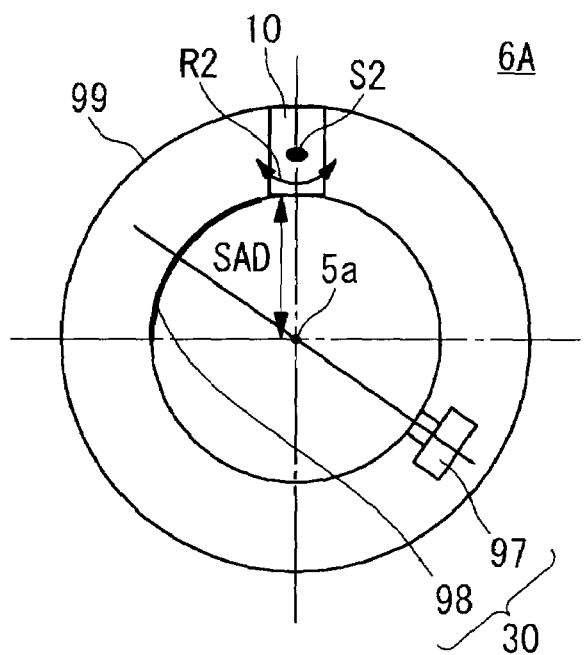
FIG. 21 is a front view showing a configuration of a rotary drum (a treatment gantry) in the second embodiment of the radiotherapy apparatus of the present invention.

FIG. 20 is a side view showing the configuration in the second embodiment of the radiotherapy apparatus of the present invention. And, FIG. 21 is a front view showing a configuration of a rotary drum (a gantry for treatment) in the second embodiment of the radiotherapy apparatus of the present invention.

In a radiotherapy apparatus 6A in this embodiment, a treatment X-ray head 10, a treatment X-ray source (a CT X-ray tube) 97 and a sensor array 98 are mounted on a rotary drum (treatment gantry) 99. That is, the structure of the entire apparatus is such that the X-ray head 10 is placed on the upper portion of the drum of the X-ray CT inspecting unit of the rotary type, which is the real time imager 30 in the first embodiment. The rotational center of the rotary drum (treatment gantry) 99 is the isocenter 5a. The X-ray head 10 is constituted by the electron linac of 4 MeV to 10 MeV, and can be swung around the two axes (the first swing axis S1 and the second swing axis S2) as shown in the figures. That is, due to those head swing operations, in addition to the isocentric irradiation around the rotational axis of the rotary drum, the two-axis non-isocentric irradiation can be carried out. Incidentally, the head swing around the second swing axis S2 contains the collimation angle correction associated with the rotation of the rotary drum. On the other hand, the collimation angle correction with regard to the head swing around the first swing axis S1 is not required.

The treatment X-ray source (the CT X-ray tube) 97 and the sensor array 98 are respectively placed at the positions where they do not interfere with the X-ray head 10 for the treatment. The treatment X-ray source (the CT X-ray tube) 97 and the sensor array 98 face on each other. The sensor array 98 for detection is used for the X-ray and it is a multiple-row sensor of a multi array (Multi Row) type. In the X-ray CT and PET, the real time image re-configuration computing process of a high speed is performed on real time imaging.

THIRD EMBODIMENT

A third embodiment of the present invention will be described below with reference to FIG. 22.

In this embodiment, the explanations of the portions overlapping with those of the first and second embodiments are omitted.

Figure 22:
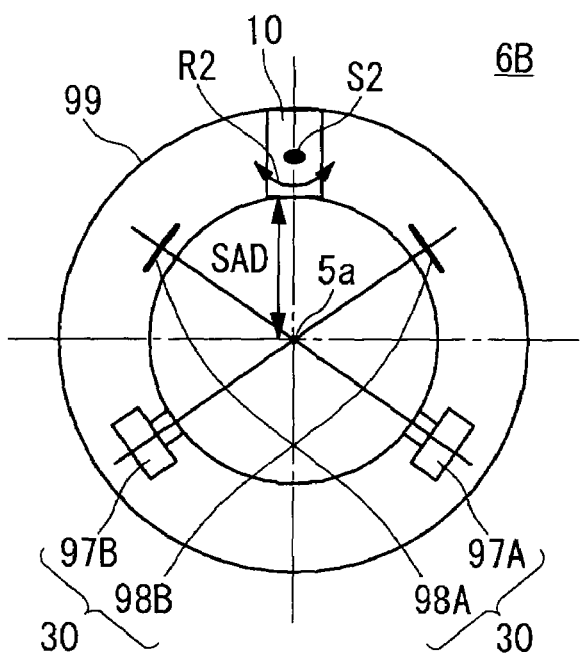
FIG. 22 is a front view showing a configuration of a rotary drum (a treatment gantry) in the second embodiment of the radiotherapy apparatus of the present invention.

FIG. 22 is a front view showing the configuration of the rotary drum (the treatment gantry) in the third embodiment of the radiotherapy apparatus of the present invention.

A radiotherapy apparatus 6B in this embodiment includes the X-ray head 10 for the treatment and two sets of X-ray source 97A or 97B and sensor array 98A or 98B constituting the typical X-ray camera, on the rotational drum (treatment gantry) 99. Those relative positions are fixed within preset ranges. As the preset range, an angle between the sensor array 98B and the isocenter 5a and the X-ray head 10 is 60 to 20 degrees. Preferably, it is 45 to 30 degrees. This is set in accordance with the conditions that they do not have any influence on each other, they are accurately operated, and the diagnosis image having a sufficient precision is also obtained.

Differently from the second embodiment having the treatment X-ray source (the CT X-ray tube) and the sensor array, the rotary drum 99 includes two sets of X-ray source 97A or 97B and sensor array 98A or 98B constituting the typical X-ray camera. The visual line of the one set between the X-ray source and the sensor array is not coincident with that of the other set. The X-ray sources 97A, 97B are located opposite to each other with a straight line through which the X-ray head 10 and the isocenter 5a are connected between. The sensor arrays 98A, 98B are similarly configured.

Consequently, the X-ray transmission images, such as the affected part 5 within the body of the patient 4, the landmark, the small gold plate and the like, can be obtained from the two axes so that the motion of the respective portions within the body of the patient 4 can be grasped quickly and accurately. The method of carrying out the imaging process, such as DSA, using the contrast medium may be considered as the image emphasizing method of the X-ray transmission image.

Also, the sensor arrays 98A, 98B are placed on the side of the X-ray head 10. Thus, the treatment X-ray 3a, which is the very strong X-ray, is never inputted to the sensor arrays 98A, 98B.

The X-ray head 10 is constituted by the electron linac of 4 MeV to 10 MeV, and can be swung around the two axes (the first swing axis S1 and the second swing axis S2) as shown in the figure. That is, those head swing operations enable the non-isocentric irradiation around the two axes, in addition to the isocentric irradiation around the rotational axis of the rotary drum. The head swing operation around the second swing axis S2 contains the collimation angle correction associated with the rotation of the rotary drum. On the other hand, the collimation angle correction with regard to the head swing operation around the first swing axis S1 is not required.

FOURTH EMBODIMENT

A fourth embodiment of the present invention will be described below with reference to FIG. 24.

In this embodiment, the explanations of the portions overlapping with those of the first, second and third embodiments are omitted.

Figure 24:
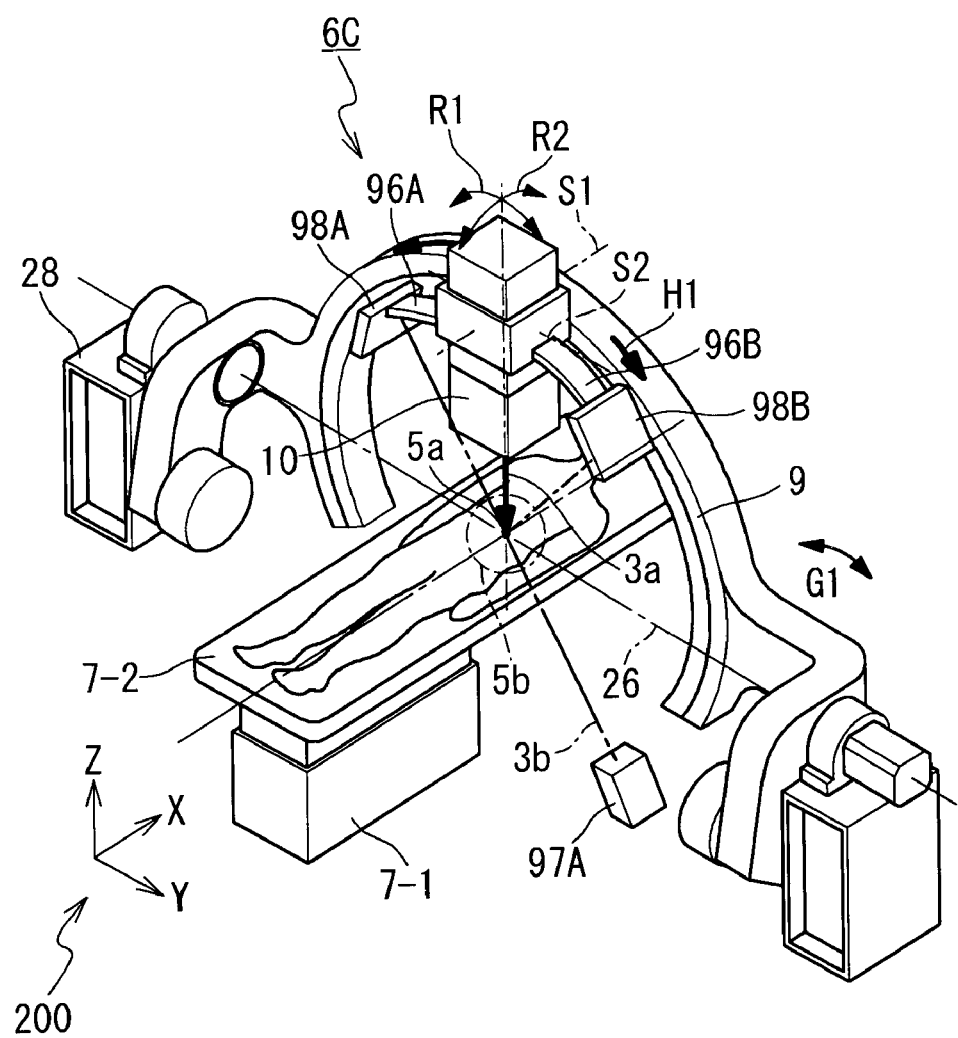
FIG. 24 is a perspective view showing a configuration of a fourth embodiment of the radiotherapy apparatus of the present invention.

FIG. 24 is a perspective view showing the configuration of the fourth embodiment of the radiotherapy apparatus of the present invention.

A radiotherapy apparatus 6C in this embodiment includes the X-ray head 10 as a real time imager (30), the X-ray sources 97A, 97B and the sensor arrays 98A, 98B.

The X-ray head 10 is movably placed on the arc guide rail 9. The X-ray sources 97A, 97B are respectively fixed on the sides different from each other, in the Y-axis direction of the X-ray head 10. The sensor arrays 98A, 98B are placed at the positions opposite to each other through the isocenter 5a in the X-ray sources 97A, 97B by fixing the relatively positional relations to the X-ray sources 97A, 97B. The X-ray sources 97A, 97B are located at the positions opposite to each other with the straight line through which the isocenter 5a and the X-ray head 10 in FIG. 24 are connected between. The sensor arrays 98A, 98B are similarly configured.

This is similar to the first embodiment in that the X-ray head 10 for the treatment is placed on the arc guide rail 9. Also, this is similar to the third embodiment in that two sets of X-ray source 97A or 97B and sensor array 98A or 98B constituting the typical X-ray camera are fixed to the X-ray head 10. Those relative positions are fixed within the preset range. As the preset range, the angle between the sensor array 98A or the sensor array 98B and the isocenter 5a and the X-ray head 10 is 60 to 20 degrees. Preferably, it is 45 to 30 degrees. This is set in accordance with the conditions that the X-ray head 10 and the X-ray sources 97A, 97B do not have any influence on each other, they are accurately operated, and the diagnosis image having a sufficient precision is also obtained.

Differently from the first embodiment in which the X-ray CT inspecting unit is installed, the second embodiment in which the treatment X-ray source (the CT X-ray tube) and the sensor array are installed in the rotary drum and the third embodiment in which the two sets of the X-ray source and the sensor array are installed in the rotary drum 99, even under all irradiation situations, the sets of the X-ray source and the sensor array are connected to the X-ray head 10 and operated so as to have the fixed positional relation to the X-ray head 10.

Consequently, in addition to the obtainment of the effects from the operations in the above-mentioned respective embodiments, the sets of the X-ray source and the sensor array have the fixed positional relation to the X-ray head 10. Thus, it is possible to largely reduce the burden on the control for obtaining the diagnosis image and the burden on the operation for the real time imager.

Also, the sensor arrays 98A, 98B are placed on the side of the X-ray head 10. Thus, the treatment X-ray 3a, which is the very strong X-ray, is never inputted to the sensor arrays 98A, 98B.

The X-ray head 10 is constituted by the electron linac of 4 MeV to 10 MeV, and can be swung around the two axes (the first swing axis S1 and the second swing axis S2) as shown in the figure. That is, those head swing operations enable the non-isocentric irradiation around the two axes, in addition to the isocentric irradiation around the rotational axis of the rotary drum.

According to the present invention, in addition to the isocentric motion in the entire X-ray head, the one-axis or two-axis head swing operation around the proper rotational center such as the inertial center or the like is performed on the head portion itself to thereby enable the pseudo non-isocentric irradiation treatment. Its effect is at the level substantially equal to the perfectly non-isocentric radiotherapy apparatus. Also, it is possible to attain the high-speed follow-up corresponding to the movement of the irradiation field caused by the breath and the cardiac beat.

According to the present invention, the non-magnetic type of the precise inspection apparatus enables the conditions, such as the irradiation position of the radiation, the irradiation time and the like, to be precisely controlled while the irradiation field is checked. Thus, this can be naturally applied to the treatment for the head portion in which the organ itself is not moved. Moreover, the radiation can be accurately irradiated to the small focus in the mobile organ such as a heart, a lung and the like. Thus, its usage can be expanded in the radiotherapy field.

According to the present invention, differently from the cantilever robot arm having many problems in view of rigidity, the radiation head supporting structure having the high strength and the high rigidity can be employed to mechanically insure the high absolute precision. Thus, the necessary effective treatment can be achieved.

The configuration, in which the general industrial robot arm having the excessive free degree largely exceeding the necessary free degree is applied to the non-isocentric irradiation treatment, has a problem in view of the safety for the patient. That is, at a time of an accident such as an erroneous operation of a robot arm or the like, there may be a possibility that the robot arm or the radiation irradiating head at the tip thereof comes in contact with the patient which brings about a surgical injury to the patient. On the contrary, since the movable range is limited, the absolute safety for the patient can be secured.

In the conventional technique, the irradiation field can not be monitored at the real time during the irradiation treatment. Thus, the irradiation based on the estimation is inevitable. However, according to the present invention, the imager, such as the typical X-ray camera, the X-ray CT, the PET, the DSA or the like enables the irradiation field to be monitored at the real time during the irradiation treatment, and thereby enables the irradiation treatment having the high reliability and safety.

Also, the image pursuit is carried out on the basis of the above-mentioned irradiation field image obtained at the real time, and the follow-up irradiation to the mobile irradiation field can be achieved.

The man-machine interface described in the embodiments of the present invention enables the radiotherapy having the excellent safety and reliability.

What is claimed is:

1. A radiotherapy apparatus comprising:
a bed which carries a subject;
a radiation irradiating head which irradiates a treatment radiation to a treatment field of said subject;
a support frame supporting said radiation irradiating head and having a gimbal structure, said support frame being installed at a position which includes an inertia center of said radiation irradiating head and through which a first axis and a second axis pass, said support frame having at least a first side, second side, third side, and fourth side;
a first head swing mechanism which is linked to said radiation irradiating head, and swings generally around the first axis at the inertia center of said radiation irradiating head, wherein said first head swine mechanism includes at least a driving shaft and swing driving servomotor installed at the first side of said support frame;
a second head swing mechanism which is linked to said radiation irradiating head, and swings generally around the second axis at the inertia center of said radiation irradiating head, wherein said second head swing mechanism includes at least a driving shaft and swing driving servomotor installed at the second side of said support frame;
an inspection unit which detects a diagnosis image containing said treatment field; and
a control unit which controls a position of said head swing mechanisms such that an irradiation field of said radiation irradiating head pursues said treatment field, based on said diagnosis image, said position of said radiation irradiating head and a swung state of said radiation irradiating head;
wherein said control unit controls said radiation irradiating head such that said treatment radiation is irradiated from said radiation irradiating head, after the positional control of said head swing mechanisms.

2. The radiotherapy apparatus according to claim 1, wherein said control unit calculates a first coordinate of said treatment field within said diagnosis image based on an image pattern, which indicates said treatment field and is preliminarily specified on said diagnosis image,
calculates a second coordinate of said irradiation field based on a position of said radiation irradiating head and a swing state of said radiation irradiating head, and
controls said head swing mechanisms such that said treatment field is contained in said irradiation field, based on said first coordinate and said second coordinate.

3. The radiotherapy apparatus according to claim 2, wherein said control unit controls said head swing mechanisms and said radiation irradiating head for a preset time interval.

4. The radiotherapy apparatus according to claim 3, wherein said precise inspection unit comprises:
a X-ray source which irradiates a diagnosis radiation to said treatment field;
a sensor array which detects a transmitted radiation of said diagnosis radiation transmitted through said subject and outputs a diagnosis image data indicating said transmitted radiation; and
an image process unit which generates said diagnosis image based on said diagnosis image data.

5. The radiotherapy apparatus according to claim 4, wherein said X-ray source is located on an opposite side of an isocenter to said sensor array, and said sensor array is placed closer to said radiation irradiating head than said X-ray source.

6. The radiotherapy apparatus according to claim 5, wherein said precise inspection unit comprises:
a plurality of sets;
wherein each of said plurality of sets includes said X-ray source and said sensor array, and
said image process unit generates said diagnosis image based on said diagnosis image data outputted from said each of said plurality of sets.

7. The radiotherapy apparatus according to claim 6, further comprises:
a guide rail which includes an orbit on which said head swing mechanisms and said radiation irradiating head are moved; and
a head circulation moving mechanism which keeps the head swing mechanisms and said radiation irradiating head at movable states and moves said head swing mechanisms and said radiation irradiating head along said guide rail.

8. The radiotherapy apparatus according to claim 7, wherein said guide rail is placed so as to straddle said bed in a width direction, and has a half-arc orbit.

9. The radiotherapy apparatus according to claim 8, further comprises:
a rail tilting mechanism which tilts said guide rail around a horizontal axis within a range of a quarter spherical shell.

10. The radiotherapy apparatus according to claim 9, wherein said head swing mechanisms swing said radiation irradiating head around each of two axes orthogonal to each other.

11. The radiotherapy apparatus according to claim 10, further comprises:
a microwave generating unit which generates a microwave; and
a waveguide which guides said microwave to said radiation irradiating head.

12. The radiotherapy apparatus according to claim 11, wherein said radiation irradiating head comprises:
an accelerating structure which accelerates an electron ray through said microwave which belongs to a C band.

13. The radiotherapy apparatus according to claim 11, wherein said radiation irradiating head comprises:
an accelerating structure which accelerates an electron ray through said microwave which belongs to an X band.

14. A radiotherapy apparatus operating method comprising the steps of:
(a) detecting a diagnosis image containing a treatment field of a subject;
(b) defining a definition region as said treatment field in said diagnosis image;
(c) recognizing said definition region;
(d) turning automatically a radiation irradiating head for irradiating a treatment radiation toward said definition region such that an irradiation field of said radiation irradiating head pursues said treatment field, said radiation irradiating head being supported by a support frame having a gimbal structure, said support frame being installed at a position which includes an inertia center of said radiation irradiating head and through which a first axis and a second axis pass, said support frame having at least a first and second side, said radiation irradiating head being in communication with a guide rail which includes an orbit on which first and second head swing mechanisms and said radiation irradiating head are moved, said head swing mechanisms and said radiation irradiating head being kept at movable states by a head circulation moving mechanism that moves said head swing mechanisms and said radiation irradiating head along said guide rail, said first head swing mechanism swings generally around the first axis at the inertia center of said radiation irradiating head, said first head swing mechanism includes at least a driving shaft and swing driving servomotor installed at the first side of said support frame, said second head swing mechanism swings generally around the second axis at the inertia center of said radiation irradiating head, said second head swing mechanism includes at least a driving shaft and swing driving servomotor installed at the second side of said support frame; and (e) irradiating said treatment radiation to said irradiation field.

15. The radiotherapy apparatus operating method according to claim 14, wherein said step (d) comprises the steps of:
(d1) calculating a first coordinate indicative of a position of an image pattern within said definition region, based on said diagnosis image;
(d2) calculating a second coordinate indicative of a position of said irradiation field, based on a position and an orientation of said radiation irradiating head; and
(d3) moving said radiation irradiating head such that said second coordinate pursue said first coordinate, based on said first coordinate and said second coordinate;
wherein said steps (d1) to (d3) are carried out automatically.

16. The radiotherapy apparatus operating method according to claim 14, further comprising the steps of:
(f) detecting another diagnosis image containing said treatment field;
(g) recognizing said definition region in said another diagnosis image;
(h) turning automatically said radiation irradiating head toward said definition region such that said irradiation field pursues said treatment field; and
(i) irradiating said treatment radiation to said irradiation field;
wherein said step (f) to said step (i) are repeated until an irradiation amount of said treatment radiation reaches a predetermined value.

17. The radiotherapy apparatus operating method according to claim 16, wherein each of said step (f) to said step (i) takes a preset time interval.

18. A radiotherapy apparatus operation method according to claim 14, wherein a rail tilting mechanism tilts said guide rail around a horizontal axis within a range of a quarter spherical shell.

19. A computer-readable medium comprising code that, when executed, causes a computer to perform the following:
receiving a detected diagnosis image containing a treatment field of a subject;
(k) recognizing a definition region defined as said treatment field in said diagnosis image;
(l) controlling a radiation irradiating head for irradiating a treatment radiation such that an irradiation field of said radiation irradiating head pursues said treatment field, said radiation irradiating head being supported by a support frame having a gimbal structure, said support frame being installed at a position which includes an inertia center of said radiation irradiating head and through which a first axis and a second axis pass, said support frame having at least a first and a second side, said radiation irradiating head being in communication with a guide rail which includes an orbit on which first and second head swing mechanisms and said radiation irradiating head are moved, said head swing mechanisms and said radiation irradiating head being kept at movable states by a head circulation moving mechanism that moves said head swing mechanisms and said radiation irradiating head along said guide rail, said first head swing mechanism swings generally around the first axis at the inertia center of said radiation irradiating head, said first head swing mechanism includes at least a driving shaft and swing driving servomotor installed at the first side of said support frame, said second head swine mechanism swings generally around the second axis at the inertia center of said radiation irradiating head, said second head swing mechanism includes at least a driving shaft and swing driving servomotor installed at the second side of said support frame; and (m) controlling said radiation irradiating head so as to irradiating said treatment radiation to said irradiation field.

20. The computer-readable medium according to claim 19, wherein said step (l) comprising the steps of:
(l1) calculating a first coordinate indicative of a position of an image pattern within said definition region, based on said diagnosis image;
(l2) calculating a second coordinate indicative of a position of said irradiation field, based on a position and an orientation of said radiation irradiating head; and
(l3) controlling said radiation irradiating head such that said second coordinate pursue said first coordinate, based on said first coordinate and said second coordinate;
wherein said steps (l1) to (l3) are carried out automatically.

21. The computer-readable medium according to claim 19, further comprising the steps of:
(n) receiving detected another diagnosis image containing said treatment field;
(o) recognizing said definition region in said another diagnosis image;
(p) controlling said radiation irradiating head such that said irradiation field pursues said treatment field; and
(q) controlling said radiation irradiating head so as to irradiating said treatment radiation to said irradiation field
wherein said step (n) to said step (q) are repeated until an irradiation amount of said treatment radiation reaches a predetermined value.

22. The computer-readable medium according to claim 21, wherein each of said step (n) to said step (q) takes a preset time interval.

23. A computer-readable medium according to claim 19, wherein a rail tilting mechanism tilts said guide rail around a horizontal axis within a range of a quarter spherical shell.

* * * * *